United States Patent
Chen et al.

(10) Patent No.: US 9,317,654 B2
(45) Date of Patent: Apr. 19, 2016

(54) SYSTEM AND METHOD TO CORRECT OUT OF PHASE ERRORS IN DNA SEQUENCING DATA BY USE OF A RECURSIVE ALGORITHM

(71) Applicant: 454 Life Sciences Corporation, Branford, CT (US)

(72) Inventors: Yi-Ju Chen, New Haven, CT (US); Chiu Tai Andrew Wong, Northford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 690 days.

(21) Appl. No.: 13/718,852

(22) Filed: Dec. 18, 2012

(65) Prior Publication Data

US 2013/0131995 A1  May 23, 2013

Related U.S. Application Data

(63) Continuation of application No. 13/043,063, filed on Mar. 8, 2011, now Pat. No. 8,364,417, which is a continuation-in-part of application No. PCT/US2007/004187, filed on Feb. 15, 2007.

(60) Provisional application No. 60/774,354, filed on Feb. 16, 2006, provisional application No. 61/319,476, filed on Mar. 31, 2010.

(51) Int. Cl.
| | |
|---|---|
| *G06F 19/22* | (2011.01) |
| *G06F 15/00* | (2006.01) |
| *C12Q 1/68* | (2006.01) |
| *G06F 19/24* | (2011.01) |

(52) U.S. Cl.
CPC .............. *G06F 19/22* (2013.01); *C12Q 1/6869* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,828,100 | B1 | 12/2004 | Ronaghi |
| 6,911,327 | B2 | 6/2005 | McMillan et al. |
| 7,133,782 | B2 | 11/2006 | Odedra |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,323,305 | B2 | 1/2008 | Leamon et al. |
| 7,335,762 | B2 | 2/2008 | Rothberg et al. |
| 2003/0219797 | A1 | 11/2003 | Zhao et al. |
| 2004/0197845 | A1 | 10/2004 | Hassibi et al. |
| 2006/0040297 | A1 | 2/2006 | Leamon et al. |
| 2007/0092872 | A1 | 4/2007 | Rothberg et al. |
| 2007/0281300 | A1 | 12/2007 | Russell et al. |
| 2009/0053724 | A1 | 2/2009 | Roth et al. |
| 2009/0176200 | A1 | 7/2009 | Wakita et al. |
| 2009/0203086 | A1 | 8/2009 | Chen et al. |

FOREIGN PATENT DOCUMENTS

| | | |
|---|---|---|
| CN | 101560564 A | 10/2009 |
| WO | WO-2005040425 A2 | 5/2005 |
| WO | WO-2007098049 A2 | 8/2007 |

OTHER PUBLICATIONS

Margulies et al. Nature vol. 437, pp. 376-380, Supplementat Figures pp. 1-12, Supplemental Materials and Methods pp. 1-34, and Supplemental Tables pp. 1-6 (2005).*
Ahmadian et al. "Pyrosequencing: History, Biochemistry and Future." *Clin. Chim. Acta.* 363(2006):83-94.
Baldi et al. "Machine Learning Foundations: The Probabilistic Network." *Bioinformatics: The Machine Learning Approach.* Cambridge, MA: MIT Press. (2000):39-57.
Brockman et al. "Quality Scores and SNP Detection in Sequencing-by-Synthesis Systems." *Genome Res.* 18(2008):763-770.
International Search Report issued in International Application No. PCT/EP2011/054817, mailed Jun. 16, 2011.
International Search Report issued in International Application No. PCT/US2007/04187, mailed Jun. 16, 2008.
Langaee et al. "Genetic Variation Analyses by Pyrosequencing." *Mutat. Res.* 573(2005):96-102.
Margulies et al. "Genome Sequencing in Microfabricated High-Density Picolitre Reactors." *Nature.* 437.7057(2005):376-380.
Margulies et al. "Supplementary Methods for the Article 'Genome Sequencing in Microfabricated High-Density Picolitre Reactors.'"*Nature.* 437.7057(2005):1-34.
Metzker. "Emerging Technologies in DNA Sequencing." *Genome Res.* 15(2005):1767-1776.
Office Action issued in Japanese Application No. 2008-555390 mailed May 11, 2012. (English Translation).
Ronaghi. "Pyrosequencing Sheds Light on DNA Sequencing." *Genome Res.* 11(2001):3-11.
Supplementary Search Report issued in European Application No. 07750981, mailed Apr. 22, 2009.

(Continued)

*Primary Examiner* — John S Brusca
(74) *Attorney, Agent, or Firm* — Cooley LLP; Ivor R. Elfiri; Christina K. Stock

(57) ABSTRACT

Provided herein are methods for correcting an error associated with phasic synchrony of sequence data generated from a population of template molecules by detecting signals generated in response to nucleotide species introduced during a sequencing reaction; generating an observed value for the signal detected from each of the nucleotide species; defining positive incorporation values and negative incorporation values from the observed values using a carry forward value and an incomplete extension value; revising the carry forward value and the incomplete extension value using a noise value derived from observed values associated with the negative incorporation values; re-defining the positive incorporation values and the negative incorporation values using the revised carry forward value and the revised incomplete extension value; and repeating the steps of revising and re-defining until convergence of the positive incorporation values and the negative incorporation values.

17 Claims, 11 Drawing Sheets

(56) References Cited

OTHER PUBLICATIONS

Communication pursuant to Article 94(3) EPC issued in European Application No. 07750981.8 dated Dec. 10, 2010.
Extended European Search Report issued in European Application No. 07750981.8 dated May 4, 2009.
Office Action issued in Chinese Application No. 200780005575.0 dated Jan. 29, 2010. (English Translation and Chinese Original).
Office Action issued in Chinese Application No. 200780005575.0 dated May 13, 2011. (English Translation and Chinese Original).
Office Action issued in Canadian Application No. 2,637,617 dated Jul. 24, 2013.
Communication issued in European Application No. 07750981.8, dated Mar. 11, 2013.
Extended European Search Report issued in European Application No. 12196383.9, mailed Mar. 7, 2013.
Office Action issued in Japanese Application No. 2008-555390, dated Jan. 21, 2013. (Japanese Original and English Abstract).

* cited by examiner

Figure 3B

CAFIE Forward $$[M(p', \lambda=0.95, \varepsilon=0.05)]$$

$$
\begin{bmatrix}
0 & 0 & 0 & 0 & 0 & 0 & 0 & 0 & 0 & 0 & 0 & 0 \\
0 & 0.95 & 0 & 0 & 0 & 0 & 0 & 0 & 0 & 0 & 0 & 0 \\
0 & 0.0025 & 0 & 0 & 0 & 0 & 0 & 0 & 0 & 0 & 0 & 0 \\
0 & 0 & 0 & 0.9049 & 0.0452 & 0 & 0 & 0 & 0 & 0 & 0 & 0 \\
0 & 0 & 0 & 0.0024 & 0 & 0 & 0 & 0 & 0 & 0 & 0 & 0 \\
0 & 0.0451 & 0 & 0 & 0 & 0.0430 & 0 & 0 & 0 & 0 & 0 & 0 \\
0 & 0.0001 & 0 & 0 & 0.8189 & 0.0001 & 0 & 0 & 0 & 0 & 0 & 0 \\
0 & 0 & 0 & 0.0860 & 0.0065 & 0 & 0 & 0 & 0 & 0 & 0 & 0 \\
0 & 0 & 0 & 0.0002 & 0 & 0.7861 & 0 & 0.0409 & 0 & 0 & 0 & 0 \\
0 & 0.0021 & 0 & 0 & 0 & 0.0021 & 0 & 0.0001 & 0 & 0.0389 & 0 & 0 \\
0 & 0 & 0 & 0 & 0.1167 & 0 & 0 & 0.7507 & 0 & 0.0001 & 0 & 0 \\
0 & 0 & 0 & 0.0061 & 0.0006 & 0 & 0 & 0.0020 & 0 & 0.7151 & 0 & 0 \\
\end{bmatrix}
$$

$$[p] = \begin{bmatrix} 0 \\ 1 \\ 0 \\ 2 \\ 0 \\ 0 \\ 1 \\ 0 \\ 3 \\ 0 \\ 1 \\ 2 \end{bmatrix} = [q] = \begin{bmatrix} 0.0000 \\ 0.9500 \\ 0.0025 \\ 1.8550 \\ 0.1337 \\ 0.0455 \\ 0.8600 \\ 0.2563 \\ 2.3591 \\ 0.0084 \\ 0.8674 \\ 1.4451 \end{bmatrix} \begin{matrix} C \\ A \\ G \\ T \\ C \\ A \\ G \\ T \\ C \\ A \\ G \\ T \end{matrix} \begin{matrix} flow\ 1 \\ flow\ 2 \\ flow\ 3 \\ . \\ . \\ . \\ flow\ i \\ . \\ . \\ . \\ . \\ flow\ 12 \end{matrix}$$

Forward Matrix Model 310

Flow 105

Figure 4A

CAFIE Inversion $$[\mathbf{p}]^{(2)} = [\mathbf{M}(\mathbf{p'}^{(1)}, \lambda = 0.95, \varepsilon = 0.05)]^{-1} [\mathbf{q}]$$

Inverse Matrix Model 320

Flow 105

$$\begin{bmatrix} 0 \\ 1 \\ 0 \\ 2 \\ 0 \\ 0 \\ 0 \\ 1 \\ 0 \\ 3 \\ 0 \\ 1 \\ 2 \end{bmatrix} = \begin{bmatrix} 0 & 0 & 0 & 0 & 0 & 0 & 0 & 0 & 0 & 0 & 0 & 0 \\ 1.0502 & 0.0028 & 0.0000 & -0.0000 & 0.0499 & 0.0000 & -0.0000 & 0.0024 & -0.0000 & 0.0000 & 0.0000 & 0.0000 \\ -0.0000 & -0.0000 & 0.0000 & -0.0000 & -0.0000 & -0.0618 & -0.0000 & -0.0000 & 0.0034 & -0.0056 & 0.0000 & 0.0000 \\ 0.0000 & 0.0000 & 1.0954 & 0.0029 & 0.0000 & 0.0000 & 0.1032 & -0.0000 & 0.0000 & 0.0000 & 0.0000 & 0.0000 \\ -0.0000 & 0.0000 & -0.0000 & -0.0000 & -0.0000 & -0.0000 & -0.0000 & -0.0000 & 0.0000 & -0.0000 & 0.0000 & 0.0000 \\ 0.0000 & 0.0000 & 0.0000 & -0.0000 & -0.0000 & -0.0000 & -0.0000 & -0.0000 & -0.0000 & -0.0000 & 0.0000 & 0.0000 \\ 0 & 0 & 0 & 0 & 0 & 0 & 0 & 0 & 0 & 0 & 0 & 0 \\ -0.0002 & -0.0000 & -0.0003 & -0.0002 & -0.0000 & 1.2307 & -0.0000 & -0.0000 & -0.0671 & -0.0000 & -0.0002 & 0.0000 \\ 0 & 0 & 0 & 0 & 0 & 0 & 0 & 0 & 0 & 0 & 0 & 0 \\ -0.0000 & -0.0000 & -0.0005 & 0.0693 & 0.0002 & 0.0000 & -0.0001 & 1.2682 & -0.0000 & -0.0000 & -0.0002 & 0.0000 \\ 0 & 0 & 0 & 0 & 0 & 0 & 0 & 0 & 0 & 0 & 0 & 0 \\ 0.0000 & 0.0000 & 0.0001 & 0.0000 & 0.0000 & -0.1913 & -0.0007 & 0.0000 & 1.3424 & 0.0000 & 1.3943 & 0.0000 \\ 0.0000 & 0.0000 & -0.0165 & -0.0001 & -0.0000 & -0.0002 & 0.0743 & -0.0000 & -0.0037 & & & \end{bmatrix} \begin{bmatrix} 0.0000 \\ 0.9500 \\ 0.0025 \\ 1.8550 \\ 0.1337 \\ 0.0455 \\ 0.8600 \\ 0.2563 \\ 2.3591 \\ 0.0084 \\ 0.8674 \\ 1.4451 \end{bmatrix} \begin{matrix} flow\ 1 \\ flow\ 2 \\ flow\ 3 \\ . \\ . \\ . \\ flow\ i \\ . \\ . \\ . \\ flow\ 12 \end{matrix}$$

[q]

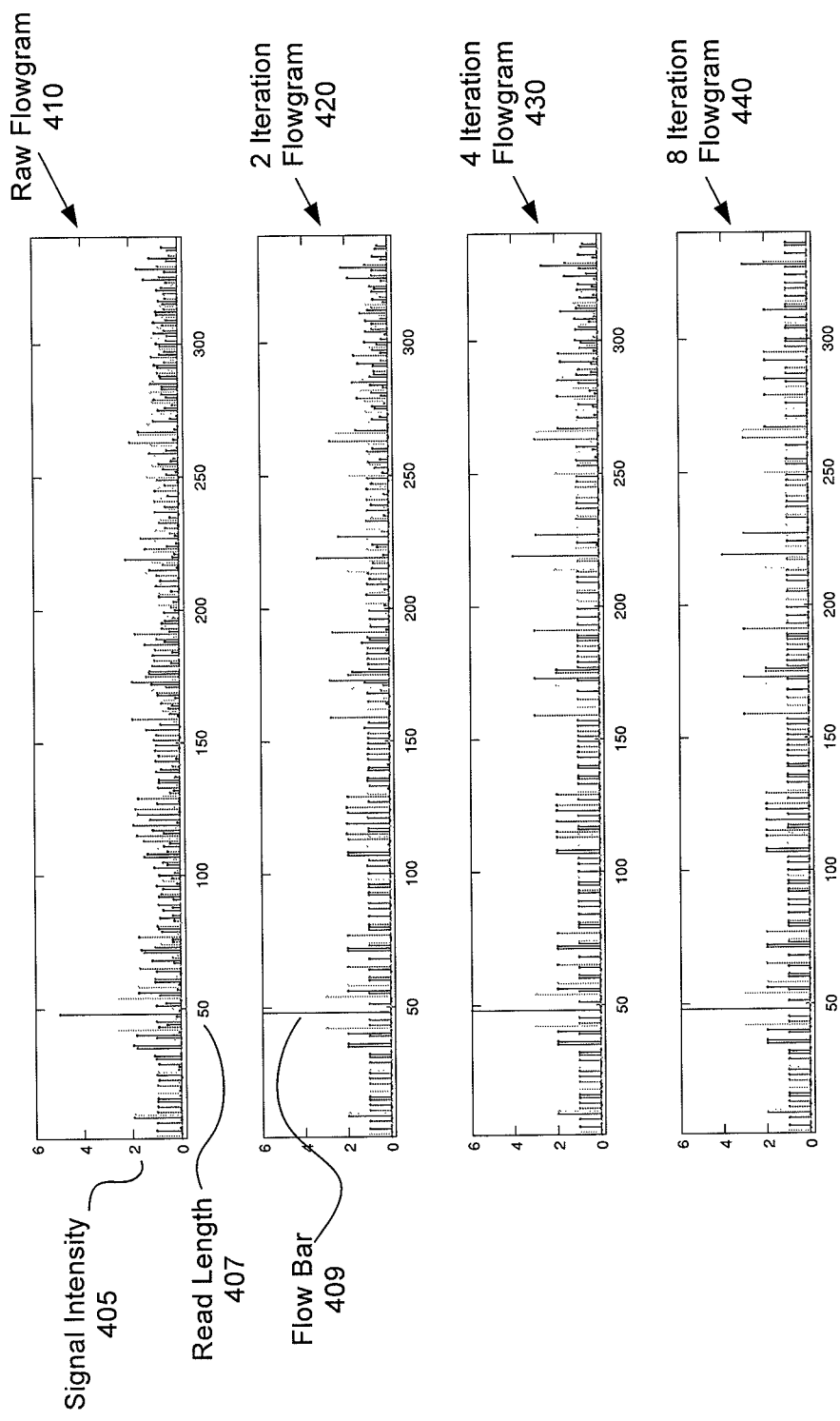

SYSTEM AND METHOD TO CORRECT OUT OF PHASE ERRORS IN DNA SEQUENCING DATA BY USE OF A RECURSIVE ALGORITHM

RELATED APPLICATIONS

The present application is a continuation of U.S. patent application Ser. No. 13/043,063, filed Mar. 8, 2011, which claims priority from U.S. Provisional Patent Application Ser. No. 61/319,476, titled "System and Method to Correct Out of Phase Errors in DNA Sequencing Data By Use of a Recursive Algorithm", filed Mar. 31, 2010 and is a Continuation in Part from PCT Patent Application Serial No. PCT/US2007/004187, titled "System and Method for Correcting Primer Extension Errors in Nucleic Acid Sequence Data", filed Feb. 15, 2007, which claims priority from U.S. 60/774,354, filed Feb. 16, 2006, each of which is hereby incorporated by reference herein in its entirety for all purposes.

FIELD OF THE INVENTION

The present invention relates to the field of molecular biology. More specifically, the invention relates to a recursive method to correct phasic synchrony errors in nucleic acid sequence data generated by what are generally referred to as "Sequencing-by-Synthesis" (SBS) techniques.

BACKGROUND OF THE INVENTION

Sequencing-by-synthesis (SBS) generally refers to methods for determining the identity or sequence composition of one or more nucleotides in a nucleic acid sample, wherein the methods comprise the stepwise synthesis of a single strand of polynucleotide molecule complementary to a template nucleic acid molecule whose nucleotide sequence composition is to be determined. For example, SBS techniques typically operate by adding a single nucleic acid (also referred to as a nucleotide) species to a nascent polynucleotide molecule complementary to a nucleic acid species of a template molecule at a corresponding sequence position. The addition of the nucleic acid species to the nascent molecule is generally detected using a variety of methods known in the art that include, but are not limited to what are referred to as pyrosequencing which may include enzymatic or electronic (i.e. pH detection with ISFET or other related technology) detection strategies or fluorescent detection methods that in some embodiments may employ reversible terminators. Typically, the process is iterative until a complete (i.e. all sequence positions are represented) or desired sequence length complementary to the template is synthesized. Some examples of SBS techniques are described in U.S. Pat. Nos. 6,274,320, 7,211,390; 7,244,559; 7,264,929; and 7,335,762 each of which is hereby incorporated by reference herein in its entirety for all purposes.

In some embodiments of SBS, an oligonucleotide primer is designed to anneal to a predetermined, complementary position of the sample template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide specie that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. As described above, incorporation of the nucleotide species can be detected by a variety of methods known in the art, e.g. by detecting the release of pyrophosphate (PPi) enzymatically or electronically (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include but are not limited to mass tags and fluorescent or chemiluminescent labels. In typical embodiments, unincorporated nucleotides are removed, for example by washing. In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, primer extension, signal acquisition, and washing result in a determination of the nucleotide sequence of the template strand.

In typical embodiments of SBS, a large number or population of substantially identical template molecules (e.g. $10^3$, $10^4$, $10^5$, $10^6$ or $10^7$ molecules) are analyzed simultaneously in any one sequencing reaction, in order to achieve a signal which is strong enough for reliable detection. What is referred to as "homogeneous extension" of nascent molecules associated with substantially all template molecules in a population of a given reaction is required for low signal-to-noise ratios. The term "homogeneous extension", as used herein, generally refers to the relationship or phase of the extension reaction where each member of a population of substantially identical template molecules described above are homogenously performing the same step in the reaction. For example, each extension reaction associated with the population of template molecules may be described as being in phase (also sometime referred to as phasic synchrony or phasic synchronism) with each other when they are performing the same reaction step at the same sequence position for each of the associated template molecules.

However, those of ordinary skill in the related art will appreciate that a small fraction of template molecules in each population loses or falls out of phasic synchronism with the rest of the template molecules in the population (that is, the reactions associated with the fraction of template molecules either get ahead of, or fall behind, the other template molecules in the sequencing reaction run on the population (some examples are described in Ronaghi, M., Pyrosequencing sheds light on DNA sequencing. Genome Res. 11, 3-11 (2001), which is hereby incorporated by reference herein in its entirety for all purposes). For example, the failure of the reaction to properly incorporate of one or more nucleotide species into one or more nascent molecules for extension of the sequence by one position results in each subsequent reaction being at a sequence position that is behind and out of phase with the sequence position of the rest of the population. This effect is referred to herein as "incomplete extension" (IE). Alternatively, the improper extension of a nascent molecule by incorporation of one or more nucleotide species in a sequence position that is ahead and out of phase with the sequence position of the rest of the population is referred to herein as "carry forward" (CF). The combined effects of CF and IE are referred to herein as CAFIE.

With respect to the problem of incomplete extension, there may be several possible mechanisms that contribute to IE that may occur alone or in some combination. One example of a possible mechanism that contributes to IE may include a lack of a nucleotide species being presented to a subset of template/polymerase complexes. Another example of a possible mechanism that contributes to IE may include a failure of a subset of polymerase molecules to incorporate a nucleotide species which is properly presented for incorporation into a nascent molecule. A further example of a possible mechanism that contributes to IE may include the absence of polymerase activity at template/polymerase complexes.

An example of yet another mechanism that can account, at least in part, for IE errors in SBS methods may include what is referred to as cyclic reversible termination (CRT) as reviewed by Metzger (Genome Res. 2005 December; 15(12): 1767-76, which is hereby incorporated by reference herein in its entirety for all purposes). In CRT, nucleotide species have a modified 3'-O group (commonly referred to as a cap, protecting group, or terminator) which prevents further extension of the nascent molecule after incorporation of single nucleotide species. These protecting groups are designed to be removable by one of a variety of methods including chemical treatment or light treatment. Upon deprotection of the 3'-O position (and creation of a 3'-OH group), the nascent molecule can be extended by another nucleotide species. However, phasic asynchronism will occur when a fraction of nascent molecules remain protected due to imperfect deprotection efficiency (incomplete deprotection). In the subsequent cycle, this fraction of nascent molecules, remaining protected, will not be extended, and will thus fall behind and out of phase with the sequence position of the rest of the population. However, subsequent deprotection steps may successfully remove at least some of the protecting groups which had previously improperly remained, causing extension to resume, and creating signals from nascent molecules and continue to be out of phasic synchrony with the rest of the population. Those of ordinary skill in the art will appreciate that other factors that contribute to IE may exist and thus are not limited to the examples provided above.

The systems and methods of the presently described embodiments of the invention are directed to the correction IE errors that may arise from any such single or combined causes or mechanisms. For instance, the correction of IE errors caused by a coupling of incomplete deprotection and subsequent successful deprotection is one object of the present invention.

With respect to the problem of CF, there may be several possible mechanisms that contribute to CF that may occur alone or in some combination. For example, one possible mechanism may include excess nucleotide species remaining from a previous cycle. This can occur because the washing protocol performed at the end of a cycle will remove the vast majority, but not necessarily all, of the nucleotide species from the cycle. In the present example a result could include a small fraction of an "A" nucleotide species present in a "G" nucleotide species cycle, leading to extension of a small fraction of the nascent molecule if a complementary "T" nucleotide species is present at the corresponding sequence position in the template molecule. Another example of a possible mechanism causing a carry forward effect may include polymerase error, such as the improper incorporation of a nucleotide species into the nascent molecule that is not complementary to the nucleotide species on the template molecule.

An example of yet another mechanism that can account, at least in part, for CF in SBS methods include cyclic reversible termination (CRT) as reviewed by Metzger (Genome Res. 2005 December; 15(12):1767-76, incorporated by reference above). In the present example, as described above with respect to IE a preparation of 3'-O protected nucleotide species may be employed where some fraction of the nucleotide molecules will lack a protecting group, or have lost the protecting group. Loss of the protecting group may also occur during the sequencing process prior to the intended deprotecting step. Any such lack of a deprotecting group will cause some nascent molecules to be extended by more than one nucleotide species at a time. Such improper multiple extension of a fraction of nascent molecules cause them to move ahead in sequence position and out of phase with the sequence position of the rest of the population. Thus, unprotected nucleotides, and/or prematurely deprotected nucleotides, may contribute, at least in part, to CF in SBS methods involving CRT.

The systems and methods of the presently described embodiments of the invention are directed to the correction of CF errors that may arise from any such single or combined causes or mechanisms. For example, the correction of CF errors that arise due to a lack of protecting groups is one object of the present invention.

Further, the systems and methods of the presently described embodiments of the invention are directed to the correction of both IE errors and CF errors, wherein both types of errors may occur in some combination for a population in the same sequencing reaction. For example, IE and CF may each arise from single or combined causes or mechanisms as described above.

Those of ordinary skill will appreciate that a potential for both IE and CF errors may occur at each sequence position during an extension reaction and thus may have cumulative effects evident in the resulting sequence data. For example, the effects may become especially noticeable towards the end of a "sequence read". The term "read" or "sequence read" as used herein generally refers to the entire sequence data obtained from a single nucleic acid template molecule or a population of a plurality of substantially identical copies of the template nucleic acid molecule.

Further, IE and CF effects may impose an upper limit to the length of a template molecule that may be reliably sequenced (sometimes referred to as the "read length") using SBS approaches, because the quality of the sequence data decreases as the read length increases.

For example, one method of SBS may generate sequence data comprising over 25 million sequence positions in a typical run with what is referred to as a "Phred" quality score of 20 or better (a Phred quality score of 20 infers that the sequence data is predicted to have an accuracy of 99% or higher). While the overall sequencing throughput with Phred 20 quality for the SBS method is significantly higher than that of sequence data generated by what is known to those in the art as Sanger sequencing methods that employ a capillary electrophoresis technique, it is currently at the cost of substantially shorter read lengths for the SBS method (Margulies et al., 2005, *Nature* 437: 376-80, which is hereby incorporated by reference herein in its entirety for all purpose). Thus, increasing the upper limit of the read lengths by avoiding or correcting for degradation of the sequence data produced by IE and CF errors would result in an increase in the overall sequencing throughput for SBS methods.

Therefore, it is desirable to provide systems and methods directed to correcting for IE and/or CF errors in sequence data produced by sequencing-by-synthesis methods of nucleic acid sequencing.

A number of references are cited herein, the entire disclosures of which are incorporated herein, in their entirety, by reference for all purposes. Further, none of these references, regardless of how characterized above, is admitted as prior art to the invention of the subject matter claimed herein.

SUMMARY OF THE INVENTION

Embodiments of the invention relate to the determination of the sequence of nucleic acids. More particularly, embodiments of the invention relate to recursive methods and systems for correcting phasic synchrony errors in data obtained during the sequencing of nucleic acids by SBS.

An embodiment of a method for correcting an error associated with phasic synchrony of sequence data generated from a population of template molecules is described that comprises the steps of detecting signals generated in response to nucleotide species introduced during a sequencing reaction; generating an observed value for the signal detected from each of the nucleotide species; defining positive incorporation values and negative incorporation values from the observed values using a carry forward value and an incomplete extension value; revising the carry forward value and the incomplete extension value using a noise value that is derived from observed values associated with the negative incorporation values; re-defining the positive incorporation values and the negative incorporation values using the revised carry forward value and the revised incomplete extension value; and repeating the steps of revising and re-defining until convergence of the positive incorporation values and the negative incorporation values.

In some implementations, the method repeats until convergence of the carry forward value and the incomplete extension value.

Also, a system for correcting an error associated with phasic synchrony of sequence data generated from a population of template molecules is described that comprises a sequencing instrument that detects a plurality of signals generated in response to a plurality of nucleotide species introduced during a sequencing reaction; and a computer comprising executable code stored thereon which performs a method comprising the steps of: generating an observed value for the signal detected from each of the nucleotide species; defining positive incorporation values and negative incorporation values from the observed values using a carry forward value and an incomplete extension value; revising the carry forward value and the incomplete extension value using a noise value, wherein the noise value is derived from observed values associated with the negative incorporation values; re-defining the positive incorporation values and the negative incorporation values using the revised carry forward value and the revised incomplete extension value; and repeating the steps of revising and re-defining until convergence of the carry forward value and the incomplete extension value.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 160 appears first in FIG. 1). All of these conventions, however, are intended to be typical or illustrative, rather than limiting.

FIG. 3*b* is a simplified graphical representation of one embodiment of a forward matrix calculation using the forward model of FIG. 3*a*;

FIG. 4*a* is a simplified graphical representation of one embodiment of an inverse matrix calculation using the inverse model of FIG. 3*a*;

FIG. 4*b* is a simplified graphical representation of one embodiment of results obtained using different levels of iterative correction using the inverse model of FIGS. 3*a* and 4*a*;

DETAILED DESCRIPTION OF THE INVENTION

Figure 1:
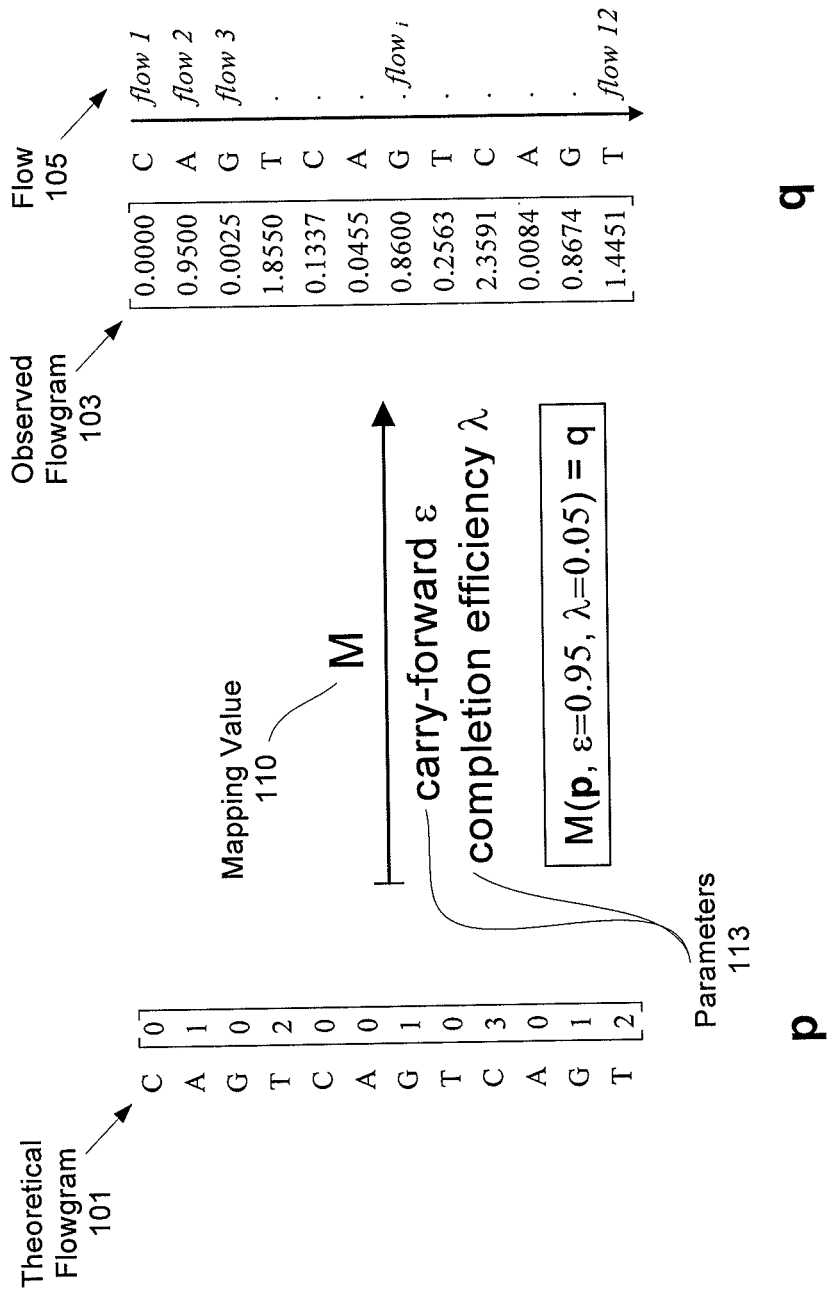
FIG. 1 is a simplified graphical representation of one embodiment of a mathematical model for converting a theoretical flowgram to an observed flowgram.

The term "flowgram" as used herein generally refers to a graphical representation of sequence data generated by SBS methods, particularly pyrophosphate based sequencing methods (also referred to as "pyrosequencing") and may be referred to more specifically as a "pyrogram".

When charted on a flowgram, a value for a detected light or other signal (e.g. pH change) for each flow may be about zero (indicating a nucleotide species in the flow was not complementary to the nucleotide species in the template at the next sequence position and thus not incorporated), or about one (indicating incorporation of exactly one nucleotide species complementary to the nucleotide species in the template was detected), or about an integer greater than one (indicating incorporation of 2 or more copies of the nucleotide species presented in the flow complementary two consecutive nucleotide species in the template were detected).

The terms "run" or "sequencing run" as used herein generally refer to a series of sequencing reactions performed in a sequencing operation of one or more template nucleic acid molecules.

The term "flow" as used herein generally refers to a serial or iterative cycle of addition of solution to an environment comprising a template nucleic acid molecule, where the solution may include a nucleotide species for addition to a nascent molecule or other reagent, such as buffers or enzymes that may be employed in a sequencing reaction or to reduce carryover or noise effects from previous flow cycles of nucleotide species.

The term "flow cycle" as used herein generally refers to a sequential series of flows where a nucleotide species is flowed once during the cycle (i.e. a flow cycle may include a sequential addition in the order of T, A, C, G nucleotide species, although other sequence combinations are also considered part of the definition). Typically, the flow cycle is a repeating cycle having the same sequence of flows from cycle to cycle.

The term "read length" as used herein generally refers to an upper limit of the length of a template molecule that may be reliably sequenced. There are numerous factors that contribute to the read length of a system and/or process including, but not limited to the degree of GC content in a template nucleic acid molecule.

The term "binary encoding list" (sometimes denoted as p' or q' as described below) as used herein generally refers to a list of nucleotide species flows comprising a binary value indicating the status of a positive or negative incorporation event for each nucleotide species (i.e. a negative incorporation event indicates that a nucleotide species was not successfully incorporated) associated with a completed sequencing run. Each nucleotide incorporation event is defined as a positive incorporation event when a value calculated from the intensity of an observed signal value during the nucleotide flow is greater than a threshold signal value or defined as a negative incorporation event when the value calculated from the intensity of an observed signal value is less than the threshold signal value. Each defined nucleotide incorporation event is then assigned a binary equivalent such that negative incorporation is represented by "0" and positive incorporation is represented by "1". For example, where the sequencing flow order is TCAG, positive incorporation events of an "A" and "G" within the first 4 flows will result in a "binary encoding list" of 0, 0, 1, 1. The terms "binary encoding list" and "binary list" are used interchangeably herein.

The term "threshold value" as used herein generally refers to a value calculated from an observed flowgram for a given sequencing run and refers to a numerical value associated with a level of signal detected from sources that are not associated with nucleotide species incorporation events (also sometimes referred to as "background signal".)

The term "nascent molecule" as used herein generally refers to a DNA strand which is being extended by the template-dependent DNA polymerase by incorporation of nucleotide species which are complementary to the corresponding nucleotide species in the template molecule.

The term "nucleotide species" as used herein generally refers to the identity of a nucleic acid monomer type including purines (Adenine, Guanine) and pyrimidines (Cytosine, Uracil, Thymine) typically incorporated into a nascent nucleic acid molecule.

The term "completion efficiency" as used herein generally refers to the percentage of nascent molecules that are properly extended during a given flow. The term "incomplete extension rate" as used herein generally refers to the ratio of the number of nascent molecules that fail to be properly extended over the number of all nascent molecules. Some embodiments of the presently described invention correct the detected signals of each flow to account for the CF and IE mechanisms described above. For example, one aspect of the invention includes calculating the extent of phasic synchronism loss for any known sequence, assuming given levels of CF and IE.

Embodiments of sequencing processes may include Sanger type techniques, techniques generally referred to as Sequencing by Hybridization (SBH), Sequencing by Ligation (SBL), or Sequencing by Incorporation (SBI) techniques. Further, the sequencing techniques may include what is referred to as polony sequencing techniques; nanopore, waveguide and other single molecule detection techniques; or reversible terminator techniques. As described above, a preferred technique may include Sequencing by Synthesis methods. For example, some SBS embodiments sequence populations of substantially identical copies of a nucleic acid template and typically employ one or more oligonucleotide primers designed to anneal to a predetermined, complementary position of the sample template molecule or one or more adaptors attached to the template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide species that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. It will also be appreciated that the process of adding a nucleotide species to the end of a nascent molecule is substantially the same as that described above for addition to the end of a primer.

As described above, incorporation of the nucleotide species can be detected by a variety of methods known in the art, e.g. by detecting the release of pyrophosphate (PPi) using an enzymatic reaction process to produce light or via detection of pH change (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include but are not limited to mass tags and fluorescent or chemiluminescent labels. In typical embodiments, unincorporated nucleotides are removed, for example by washing. Further, in some embodiments the unincorporated nucleotides may be subjected to enzymatic degradation such as, for instance, degradation using the apyrase or pyrophosphatase enzymes as described in U.S. patent application Ser. No. 12/215,455, titled "System and Method for Adaptive Reagent Control in Nucleic Acid Sequencing", filed Jun. 27, 2008; and Ser. No. 12/322,284, titled "System and Method for Improved Signal Detection in Nucleic Acid Sequencing", filed Jan. 29, 2009; each of which is hereby incorporated by reference herein in its entirety for all purposes.

In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, extension, signal acquisition, and washing result in a determination of the nucleotide sequence of the template strand. Continuing with the present example, a large number or population of substantially identical template molecules (e.g. $10^3$, $10^4$, $10^5$, $10^6$ or $10^7$ molecules) are typically analyzed simultaneously in any one sequencing reaction, in order to achieve a signal which is strong enough for reliable detection.

Also, the systems and methods of the presently described embodiments of the invention may include implementation of some design, analysis, or other operation using a computer readable medium stored for execution on a computer system. For example, several embodiments are described in detail below to process detected signals and/or analyze data generated using SBS systems and methods where the processing and analysis embodiments are implementable on computer systems.

An exemplary embodiment of a computer system for use with the presently described invention may include any type of computer platform such as a workstation, a personal computer, a server, or any other present or future computer. It will, however, be appreciated by one of ordinary skill in the art that the aforementioned computer platforms as described herein are specifically configured to perform the specialized operations of the described invention and are not considered general purpose computers. Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Celeron®, Core™, or Pentium® processor made by Intel Corporation, a SPARC® processor made by Sun Microsystems, an Athlon™, Sempron™, Phenom™, or Opteron™ processor made by AMD corporation, or it may be one of other processors that are or will become available. Some embodiments of a processor may include what is referred to as Multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows®-type operating system (such as Windows® XP, Windows Vista®, or Windows®_7) from the Microsoft Corporation; the Mac OS X operating system from Apple Computer Corp. (such as Mac OS X v10.6 "Snow Leopard" operating systems); a Unix® or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also, a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example, some commonly employed web browsers include Microsoft® Internet Explorer 8 available from Microsoft Corporation, Mozilla Firefox® 3.6 from the Mozilla Corporation, Safari 4 from Apple Computer Corp., Google Chrome from the Google™ Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Examples of a previously described embodiments are provided in PCT Patent Application Serial No., US 2007/004187, titled "System and Method for Correcting Primer Extension Errors in Nucleic Acid Sequence Data", filed Feb. 15, 2007, incorporated by reference above, and are based, at least in part, upon the discovery that a theoretical flowgram can be converted into a real life observed flowgram by a mathematical model of IE and CF. For example, a theoretical flowgram represents data generated from a sequence read that has no error from the CAFIE mechanisms described above or other types of background error. Along the same lines an observed flowgram represents data generated from a sequence read that includes some measure of the described CAFIE and other background error factors. In the present example, some or all of the error factors may be accurately approximated and applied to the theoretical flowgram model to provide a representation of real data obtained from an actual sequencing run. Further, the previously described embodiments described herein are also based, at least in part, upon the notion that one can approximate a theoretical flowgram from an observed flowgram using an inversion of a mathematical model. Thus, continuing the example from above an approximation of error may be applied to actual sequencing data represented in an observed flowgram to produce a theoretical flowgram representing the sequence composition of a target nucleic acid with all or substantially all of the error factors removed.

Some previously described embodiments correct the detected signals of each flow to account for the CF and IE mechanisms described above. For example, one aspect includes calculating the extent of phasic synchronism loss for any known sequence, assuming given levels of CF and IE.

Table 1, illustrated below, provides an example of mathematically modeled threshold values for IE and CF that provide an accuracy of 99% or better (e.g. the read is at least 99% representative of actual sequence of template molecule) for different read lengths. The predicted values presented in Table 1 illustrate the impact of CF and IE effects on sequencing accuracy for various read lengths and the extent of IE and CF error that can be tolerated to achieve a read accuracy of approximately 99%. Table 1 shows that for an uncorrected read a CF rate of no greater than 1% is permissible (assuming IE equals zero for that population) in order for a read length of about 100 sequence positions to be 99% accurate (i.e. completion efficiency of 99% or higher). Furthermore, an IE rate of no greater than 0.25% is permissible (assuming the CF rate equals zero) in order for a read length of about 100 sequence positions to be 99% accurate.

TABLE 1

| Predicted rates of error resulting in 99% accuracy at different read lengths | | | | | | |
|---|---|---|---|---|---|---|
| Read Length (bases) | 100 | | 200 | | 400 | |
| Incomplete Extension | 0.0 | 0.0025 | 0.0 | 0.0013 | 0.0 | 0.0007 |
| Carry Forward | 0.01 | 0.0 | 0.005 | 0.0 | 0.003 | 0.00 |
| Predicted Accuracy | ~99% | ~99% | ~99% | ~99% | ~99% | ~99% |

It will be understood that the values presented in Table 1 are for the purposes of illustration only and should not be considered limiting. Those of ordinary skill will appreciate that several factors may contribute to variability of values such as the genomic or reference sequences and other parameters used to formulate predictions. For example, typical embodiments of SBS methods generally achieve CF rates that range from 1-2%, while IE rates range from 0.1-0.4% (i.e. completion efficiency ranges from 99.6-99.9%). As described above, correction of CF and IE is desirable because the loss of phasic synchronism has a cumulative effect over the read length and degrades the quality of a read as read length increases.

In some previously described embodiments, values representing both CF and IE are assumed to be substantially constant across the entire read of a substantially identical template molecule population, such as for instance a population of template molecules residing within a single well of a PicoTiterPlate array or other type of array of wells such as ISFET type devices. This permits numerical correction of each sequence position across the entire read using two simple parameters "completion efficiency" and "carry forward" without any a priori knowledge of the actual sequence of the template molecule. Systems and methods of previously described embodiments have been found to be very effective for determining, and correcting for, the amounts of CF and IE occurring in a population of template molecules. For example, previous embodiments of correction have been implemented that apply a correction of the signal value detected from each flow for each population of substantially identical template molecules residing in each well to account for CF and IE.

Previously described embodiments model the lack of phasic synchronism as a nonlinear mapping:

$$M(p, \epsilon, \lambda) = q \quad \text{Equation (1):}$$

Wherein:
  M is the CAFIE mapping
  p is the theoretical flowgram [as array]
  $\lambda$ is the completion efficiency parameter
  $\epsilon$ is the carry forward parameter
  q is the observed flowgram [as array]

A theoretical flowgram can be converted into a real-life observed flowgram by use of the mapping model formula given in Equation (1) to estimate IE and CF. A model for such a mapping formula can be generated by, for example, analyzing the errors that are introduced to an observed flowgram (q) by sequencing a polynucleotide template molecule having a known sequence. An example of the mathematical model given by Equation (1) is illustrated in FIG. 1.

For example on the left hand side of FIG. 1, theoretical flowgram 101 is an illustrative representation of a theoretical flowgram (p), that shows an idealized signal strength value depicted in brackets next to its associated nucleotide species. Each idealized value of theoretical flowgram 101 is an integer or zero. In the present example, a value of "1" represents a 100% detected signal strength elicited by a single nucleotide incorporation, and "0" represents 0% signal (e.g., in a well comprising a population of 1 million substantially identical template molecules and 1 million nascent molecules, "1" represents the signal elicited when every nascent molecule is extended by a single nucleotide, "2" represents the signal elicited when every nascent molecule is extended by two nucleotides, etc.).

On the right hand side of FIG. 1, observed flowgram 103 is an illustrative representation of a detected signal strength value from an observed (or simulated) flowgram (q). Similarly, each signal strength value in flowgram 103 is depicted in brackets next to its associated nucleotide species. Also on the right hand side of FIG. 1 is flow 105 that provides a representative number representing the iterative flow sequence associated with the nucleotide species and signal values (e.g. each iteration of flow 105 represents an addition of a nucleotide species followed by a wash process). For instance, flow 1 as illustrated in FIG. 1 is associated with the "C" nucleotide species introduced in said iteration of flow 105 and a corresponds to a signal value for both theoretical flowgram 101 and observed flowgram 103.

In the example of FIG. 1 the differences in signal strength values between theoretical flowgram 101 and observed flowgram 103 for the each flow 105 iteration is indicative, at least in part, of a loss of phasic synchrony. For instance, the signal values represented in observed flowgram 103 are not integers, rather each are typically slightly higher or slightly lower than ideal value represented in theoretical flowgram 101 for the same iteration of flow 105.

Mapping model 110 represented as "M", may be estimated using known values for parameters 113. For example, parameters 113 include a $\epsilon$ (carry-forward) parameter and a $\lambda$ (completion efficiency) parameter. Parameters 113 may be employed to estimate mapping model 110 and convert the signal values of the theoretical flowgram (p) 101 into the observed values (q) 103. In the present example, the error value represented by mapping model 110 accumulates with each iteration of flow 105, and grows exponentially.

Continuing the example from above, the error represented by the error value may in theory grow exponentially with each flow. For instance, the phasicly synchronized sequencing reactions associated with each population of substantially identical template molecules become three different phasicly synchronized sub-populations after a flow iteration. The sub-populations include: a first sub-population of phasicly synchronized reactions where the nucleotide species in the flow is properly incorporated at the appropriate sequence position relative to the template molecules (e.g. no CAFIE effects); a second sub-population of phasicly synchronized reactions where improper incorporation from CF mechanisms has occurred and the reactions are ahead of the sequence position relative of the first population; and a third sub-population of phasicly synchronized reactions where improper incorporation from IE mechanisms has occurred and the reactions are behind the sequence position of the first population. In the present example, at the next flow iteration three sub-sub-populations will form from each of the three sub-populations described above, and so on. Those of ordinary skill in the related art will appreciate that at an n-th flow iteration, there will be $3^n$ populations of phasicly synchronized reactions contributing a signal at flow n.

Figure 2:
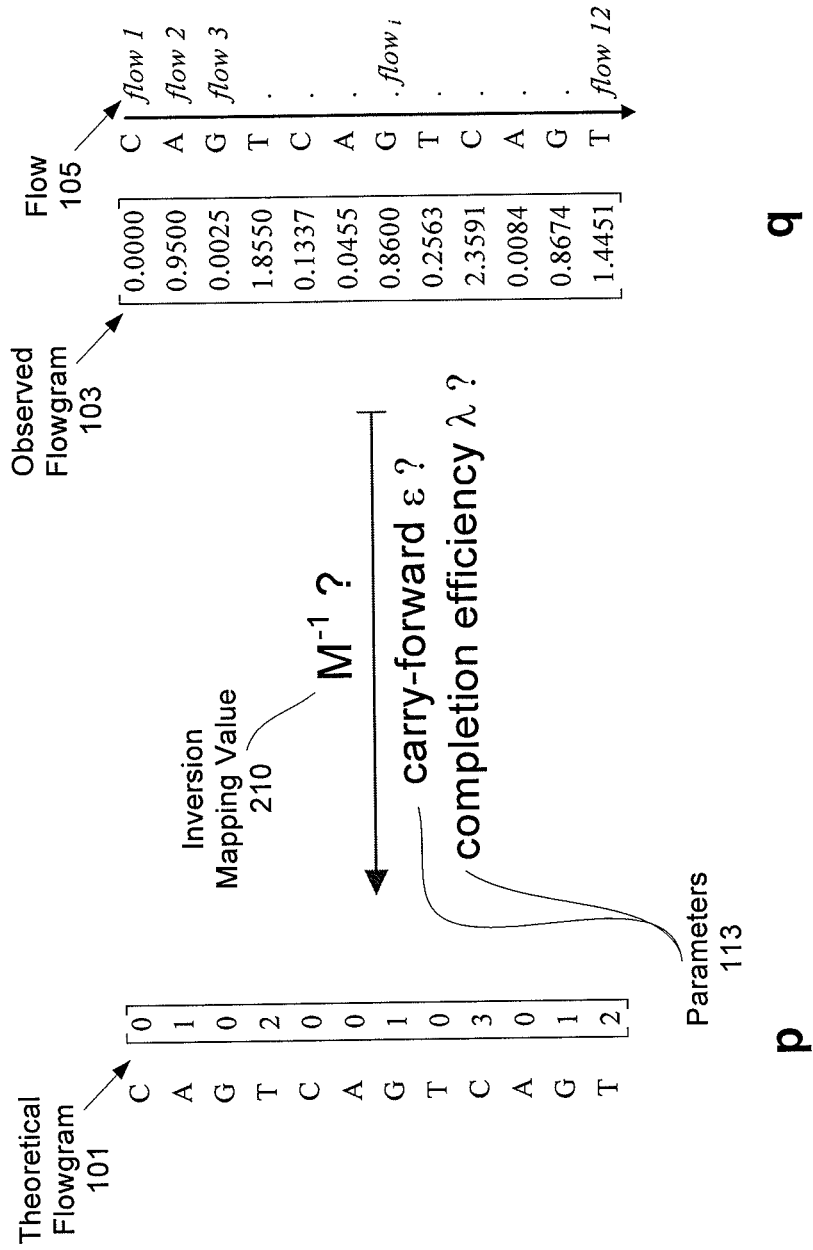
FIG. 2 is a simplified graphical representation of one embodiment of an inversion of the mapping model of FIG. 1.

Further continuing the example from above, FIG. 2 provides an illustrative representation of an inversion of mapping model 110 that is represented in FIG. 2 as inversion mapping model 210. For instance, by estimating the correct values for parameters 113 (e.g. a value for both the $\epsilon$ (carry-forward) and $\lambda$ (completion efficiency) parameters), the signal values of observed flowgram (q) 103 are inverted back to give the signal values of the theoretical flowgram (p) 101.

Those of ordinary skill in the related art will appreciate that the signal values represented in FIGS. 1 and 2 are provided for the purposes of illustration only and that a broad range of signal values are possible. Thus, they should not be considered as limiting.

Some embodiments execute the inverted mapping in two consecutive stages, (i) and (ii) outlined below:

For each nucleotide species flow i:

(i)—extension of nascent molecule through nucleotide species addition:

$$\begin{cases} q_i = \lambda \sum_j m_j p_j \\ (m_j, m_{j'}) \leftarrow (m_j, m_{j'}) + \lambda(-1, 1)m_j p_j \end{cases}$$

for all $j$ such that $N_j = N_i$ and $p_j > 0$ (ii)—extension of nascent molecule through nucleotide species leftover from a previous addition:

$$\begin{cases} q_i \leftarrow q_j + \varepsilon \sum_j m_j p_j \\ (m_j, m_{j'}) \leftarrow (m_j, m_{j'}) + \varepsilon(-1, 1)m_j p_j \end{cases}$$

for all $j$ such that $N_j = N_{i-1}$ and $p_j > 0$

Wherein:

$p_i$ is the theoretical (clean) flowgram signal value at i-th nucleotide species flow $q_i$ is the observed flowgram signal value at i-th nucleotide species flow $m_i$ is the fraction of nucleotide species molecules available for incorporation at a flowgram sequence position for the i-th nucleotide species flow $N_i$ is the i-th nucleotide species addition (A, C, G, or T)

(j, j') are pair indices such that $p_{j'}$ is the next positive value of $p_j$ on the flowgram In some embodiments, the calculations using the mapping model are executed flow-by-flow (e.g. iterations of flow 105), and updates observed flowgram (q), and the fraction of the template molecules, m, recursively through stages (i) and (ii).

Figure 3A:
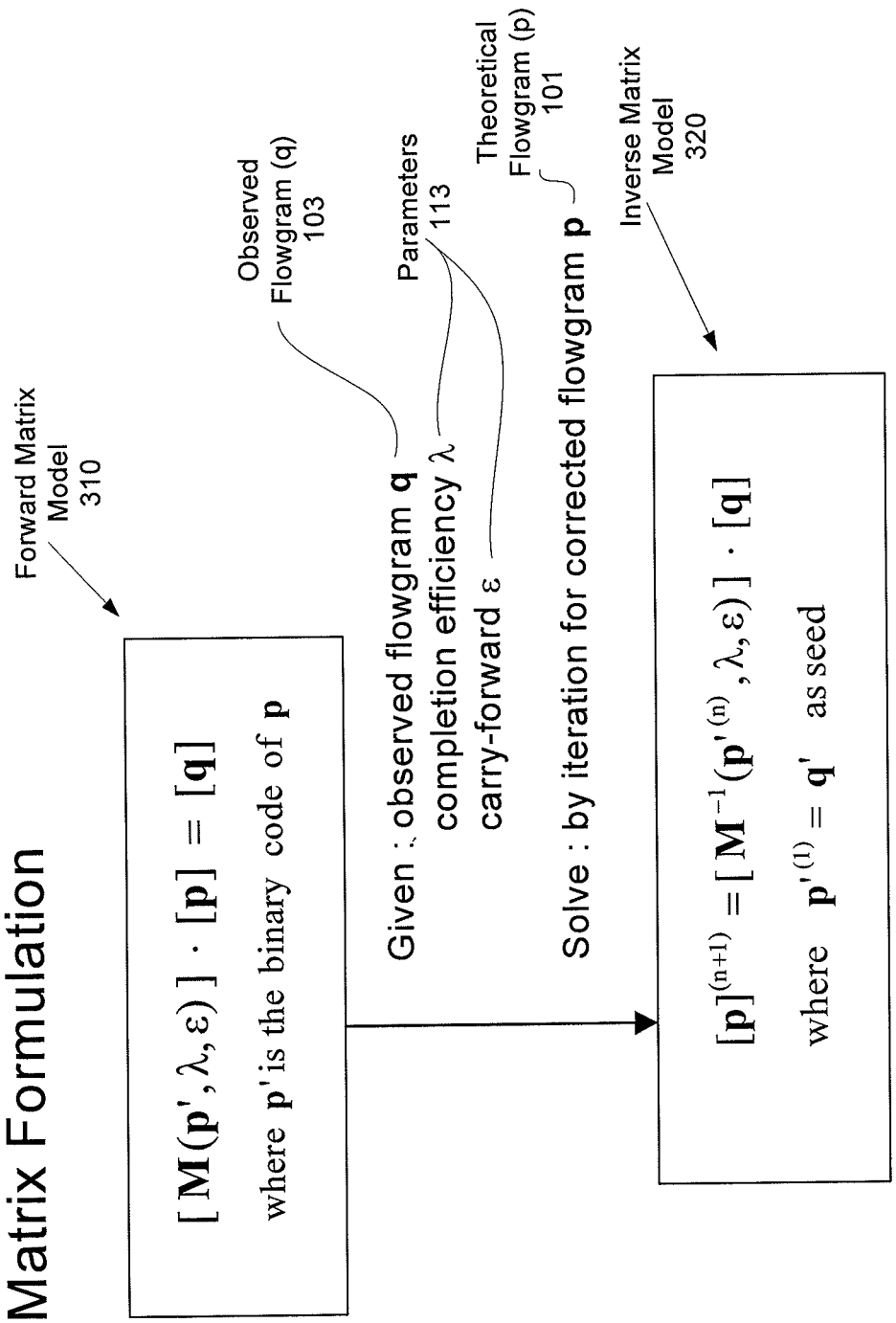
FIG. 3*a* is a simplified graphical representation of one embodiment of models for forward and inverse matrix calculations that include the mapping models of FIGS. 1 and 2.

FIG. 3A provides an illustrative example of models employed for matrix calculations. For example, as will be described in greater detail below, forward matrix model 310 may be employed to derive inverse matrix model 320. In the present example, performing matrix calculations using inverse matrix model 320 may be employed to derive estimations for parameters 113. For instance, various values for parameters 113 may be applied in the matrix calculations and evaluated for the degree of fit to observed flowgram 103. Typically, parameters 113 that provide the best fit to observed flowgram (q) 103 are determined to be good estimates for actual values of parameters 113.

Further, FIG. 3B provides an illustrative example of a forward matrix calculation using forward matrix model 310. In the present example, observed flowgram (q) 103 is generated by the matrix calculation using parameters 113 that includes a completion efficiency value $\lambda=0.95$ and a carry forward value $\epsilon=0.05$. Each row associated with an iteration of flow 105 of the matrix records the operations and results of recursive stages (i, ii) for each nucleotide species flow.

Equation (1) and the recursive stages (i, ii) can be rewritten as a matrix-array operation:

$$[M(p',\epsilon,\lambda)]*p=q \quad \text{Equation (2):}$$

wherein:

$[M(p', \epsilon, \lambda)]$ is a matrix

* is the matrix-array multiplication p' is binary encoding list of a theoretical flowgram (e.g., the flowgram p in FIG. 1, $p=[0\ 1\ 0\ 2\ 0\ 0\ 1\ 0\ 3\ 0\ 1\ 2]^t$ will be encoded as $p'=[0\ 1\ 0\ 1\ 0\ 0\ 1\ 0\ 1\ 0\ 1\ 1]^t$).

The inverse form of Equation (2) gives the inverse mapping, converting the observed flowgram (q) 103 back to theoretical flowgram (p) 101:

$$p=[M^{-1}(p',\epsilon,\lambda)]*q \quad \text{Equation (3):}$$

wherein:

$[M^{-1}(p',\epsilon,\lambda)]$ is the inverse matrix

An iterative method is used solve the inverse Equation (3), illustrated as inverse matrix model 320 in FIG. 3A, to obtain the theoretical flowgram (p) 101 for each read. This iteration is performed with a given pair of parameters 113 ($\epsilon, \lambda$) for the CAFIE inversion:

$$p^{(n+1)}=[M^{-1}(p'^{(n)},\epsilon,\lambda)]*q \quad \text{Equation (4):}$$

Wherein $p'^{(1)}=q'$ is used as the seed for the calculation.

Similar to FIG. 3B, FIG. 4A provides an illustrative example of an inverse matrix calculation using inverse matrix model 320. In the present example, theoretical flowgram (p) 101 is generated from the observed flowgram (q) 103 using parameters 113 that include on a completion efficiency value lambda=0.95 and a carry forward value epsilon=0.05.

A value of threshold is used to represent an estimation of the signal to noise ratio of the system. For example, in one implementation a fixed value, threshold=0.2, may be employed. In such an implementation, the binary encoding list q' associated with a flowgram q encodes a value "1" when the flowgram value q is greater than 0.2, and encodes a value "0" when the flowgram value q is less than or equal to 0.2. In the present example, the threshold value 0.2 is an estimation of the signal to noise ratio as described above.

Alternatively, some implementations may employ a threshold value in the range between 0 and 1, such as 0.05, 0.1, or 0.3. Thus, the observed flowgram (q) 103 can be inverted back to the clean theoretical flowgram (p) 101 through Equation (4), for a given pair of parameters 113 ($\epsilon$, $\lambda$). In many implementations, a single iteration of flowgram inversion can generally suffice. In some implementations it may be desirable to perform, 2, 3, or more iterations of flowgram inversion where the accuracy of the flowgram representation may be improved with each iteration, particularly for longer read lengths, until convergence of the calculation on a solution with a desired quality. In a preferred embodiment, 1 or 2 iterations of flowgram inversion may be performed in the interest of computational efficiency. Also, some embodiments of the invention implemented by computer code may enable a user selection of a number of iterations to perform and/or serially perform each iteration in response to a user selection. For example, a user may perform selections using methods known in the art such as inputting values in one or more fields or selection of buttons presented in a GUI. In the present example, a user may input a value indicating a number of iterations to perform and/or the user may select a button to execute an iteration of the invention. Further, the user may select an indication of data quality where the invention iterates until the level of data quality is achieved.

FIG. 4B provides an illustrative example of how results may be improved in successive numbers of iterations using the method of Equation (4). Raw flowgram 410 illustrates an embodiment of observed flowgram (q) 103 having parameter values 113 that include a completion efficiency value $\lambda=0.997$ and carry-forward value $\epsilon=0.03$ from 336 flow iterations of nucleotide species addition each iteration represented by flow bar 409. For instance, each flow bar 409 is representative of a flow of a nucleotide species and each species may be specifically represented by a color or pattern of bar 409. Further, the detected or corrected signal value associated with each flow is represented by the height of bar 409 relative to the scale given by signal intensity 405.

Those of ordinary skill in the related art will appreciate that there is a high degree of variability in raw flowgram 410 with respect to the value of signal intensity 405 for flow bars 409, particularly for read length greater than 50 sequence positions relative to the scale given by read length 407. In other words, signal values for the majority of flow bars 409 do not include signal values that are integers. 2 iteration flowgram 420 illustrates the same embodiment of observed flowgram (q) 103 after 2 iterations of correction using an embodiment of the invention. The consistency of signal intensity 405 for flow bars 409 is improved particularly for flow bars 409 at read length 407 position 150 or less. Similarly improvements of data quality are demonstrated in 4 iteration flowgram 430 and 8 iteration flowgram 440 respectively where flowgram 440 illustrates that substantially all flow bars 409 show consistency and integer values.

In some embodiments, estimations of values for parameters 113 may be determined using Equation (4). For example, the best-fitting value for the completion efficiency parameter ($\lambda$) may be determined by performing test calculations using Equation (4) inputting different values for the completion efficiency parameter while using a fixed value for the CF parameter. In the present example, values of $\lambda=1$, 0.999, 0.998, . . . , 0.990, with a fixed CF value $\epsilon=0$ may be successively employed and results for each obtained. In different embodiments, the 0.001 interval between input $\lambda$ values may be replaced by other intervals, such as, for instance, interval values of 0.05, 0.01, 0.005, 0.001, 0.0005, 0.0001, or the like.

Continuing with the present example, if any signal value 405 for a flow bar 409 in a computed theoretical flowgram (p) falls below zero after solving Equation (4) using an input value for $\lambda$, then that $\lambda$ value is declared as the value of the best-fitting completion efficiency parameter. Once the best fitting value of $\lambda$ is determined use of subsequently smaller $\lambda$ values will result in what is referred to as "over-fitting" and produce artificially-negative flow signals. Also in the present example, a corrected signal value 405 for some flow bar 409 at a sequence position after a long series of flow bars 409 representing homopolymers (e.g. a series of sequence positions comprising the same nucleotide species) may fall below zero. This zero-crossing point is illustrated in oval 503 in FIG. 5, and the best-fit completion efficiency is denoted as $\lambda^*$ hereafter.

Figure 5:
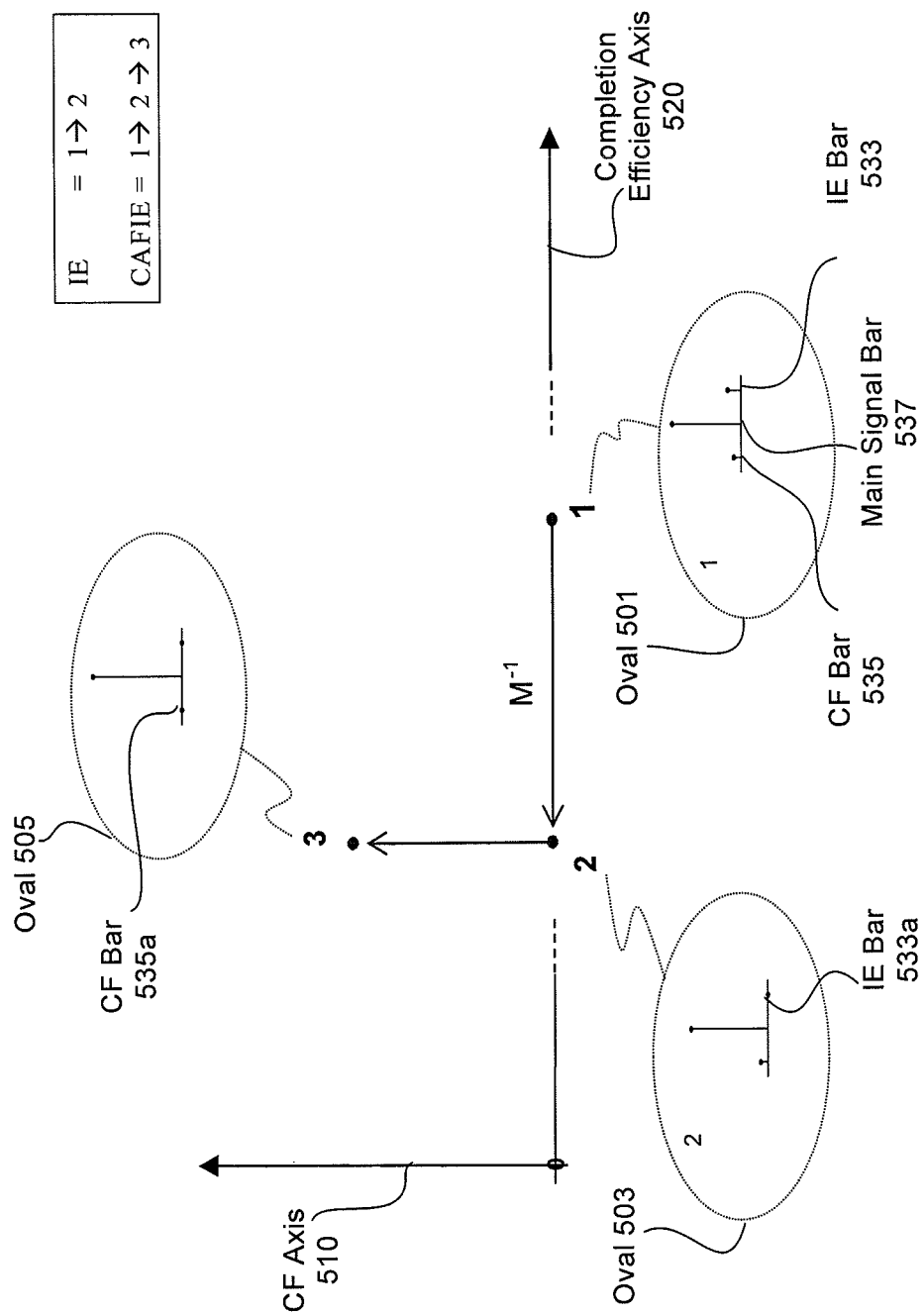
FIG. 5 is a simplified graphical representation of one embodiment of results of the CAFIE error correction method of the presently described invention.

Likewise, in some embodiments the effect of CF may be addressed by a similar approach. For example, values for the CF parameter may be tested that, for instance, may include values of $\epsilon=0$, 0.0025, 0.005, 0.0075, 0.01, . . . , 0.04 with the completion efficiency parameter $\lambda$ fixed at the previously found value $\lambda^*$. This is illustrated in FIG. 5, as step 2→3, where oval 503 indicates the starting position 2($\epsilon, \lambda$)=(0, $\lambda^*$). In the present example, the 0.0025 interval between input values for $\epsilon$ is presented for the purpose of illustration and can be replaced by other small interval values such as, for instance, interval values of 0.05, 0.01, 0.005, 0.001, 0.0005, 0.0001, 0.00001, or the like. If any signal value 405 for a flow bar 409 in a computed theoretical flowgram (p) falls below zero after solving Equation (4) using an input value for $\epsilon$ (e.g., any signal value 405 for a flow bar 409 other than the signal value 405 for flow bars 409 that fell below zero during the search along the $\lambda$ path), then that $\epsilon$ value is declared as the value of the best-fitting CF parameter. Once the best fitting value of $\epsilon$ is determined use of subsequently larger values will result in over-fitting and produce artificially negative flow signals. Also in the present example, a corrected signal value 405 for some flow bar 409 at a sequence position before a long series of flow bars 409 representing homopolymers may fall below zero. This zero-crossing point is illustrated in oval 505 in FIG. 5, and the best-fit CF is denoted as $\epsilon^*$ hereafter.

FIG. 5 provides an illustrative example where, for instance, the abscissa represents completion efficiency axis 520, and the ordinate represents CF axis 510. Graphs within ovals 501, 503, and 505 each represent steps as described above and comprise an exemplary portion of a flowgram showing three signals. For instance, the center bar represents the main signal bar 537, flanked by the left minor signal (CF bar 535), and the right minor signal (IE bar 533). Oval 501 illustrates the step of an original observed flowgram (q) 103, where main signal bar 537 is diminished by phasic asynchronism, and the minor signals of CF bar 535 and IE bar 533 represent noise caused by phasic asynchronism. Oval 503 represents a step when IE has been corrected, where the signal associated with IE bar 533a is eliminated, and the center main signal bar 537 is increased accordingly. As described above, the point where IE has been corrected may, for instance, include the zero-crossing point for the best-fit completion efficiency parameter and denoted as $\lambda^*$. Oval 505 represents a further step where CF has been corrected illustrated by the elimination of signal associated with CF bar 535a, and the center main signal bar 537 is increased accordingly. As described above, the point where CF has been corrected may, for instance, include the zero-crossing point for the best-fit completion efficiency parameter and denoted as $\epsilon^*$. Oval 505 illustrates the result of correction which is an approximation of the theoretical, expected flowgram from which noise attributable to phasic asynchronism errors has been substantially removed.

Thus, since the amounts of CF and IE, as well as the underlying template molecule sequence p, are unknown a priori, the methods of the invention can be used in a complete de-novo analysis mode. No prior knowledge of the polymerase incorporation efficiency (i.e. $\lambda$) or the effectiveness of the nucleotide wash-out (i.e. $\epsilon$) is necessary; nor are any reference nucleotide sequences required to perform the inversion.

In some embodiments, the search process for parameter estimation described above constructs a matrix [M] through stages (i, ii) at every input search interval of $\epsilon$ and $\lambda$, which is limiting from a computational efficiency perspective. Such limitations may be overcome, at least in part, by employing approximations on the matrix construction operation. For example, one can avoid re-constructing the matrix at every search interval and hence greatly improve the computational speed. Two such methods are described below:

Method 1:

At small values of $\epsilon$ and $(1-\lambda)$ (e.g., $(1-\lambda)<=0.001$ and $\epsilon<=0.0025$), the matrix [M] is decomposed, and approximated into a form:

$$[M(p',\epsilon,\lambda)] \sim [L(p',\Delta\lambda)]^{\phi} * [U(p',\Delta\epsilon)]^{\overline{\omega}} \qquad \text{Equation (5):}$$

wherein:
  $\Delta\epsilon=0.0025$ and $\Delta\lambda=0.001$, are the intervals in the $\epsilon$- and $\lambda$-axis, respectively.

φ and ω̄ are the matrix powers, with the properties of ω̄~ε/Δε and φ~(1−λ)/Δλ.

[L(p', Δλ)] is a lower diagonal matrix, which models the effect of IE at a small deficiency Δλ.

[U(p', Δλ)] is an upper diagonal matrix, which models the effect of CF at small deficiency Δε.

Through this decomposition, Equation (5) constructs the lower diagonal matrix L and upper diagonal matrix U only once along the search path, and the degrees of incompletion and carry-forward at the search grid, (ε, λ), are modeled by the powers of the matrices, (ω̄, φ). The small values in the search intervals, Δε=0.0025 and Δλ=0.001, may be replaced by other small values, such as, for example, 0.05, 0.01, 0.005, 0.001, 0.0005, 0.0001, or the like.

Instead of searching on (ε, λ)-grids previously exhibited, the method here stages through a set of (ω̄, φ)-grids, which are preferably positive integers to facilitate the computations of matrix powers. The best-fit (ω̄*, φ*) are defined at the zero-crossing condition; the corresponding completion efficiency and CF parameters are $$\lambda^* = (1 - \phi^* \Delta \lambda) \text{ and } \epsilon^* = \overline{\omega}^* \Delta \epsilon.$$

Method 2:
Following Equation (5) at small ε and (1−λ) cases, the lower and upper diagonal power matrices, $[L]^\phi$ and $[U]^{\overline{\omega}}$, are further approximated by $$[L]^\phi \equiv ([I]+[l])^\phi \sim [I]+\phi[l] \quad \text{Equation (6):}$$

$$[U]^{\overline{\omega}} \equiv ([I]+[u])^{\overline{\omega}} \sim [I]+\overline{\omega}[u] \quad \text{Equation (7):}$$

wherein:
[I] is the identity matrix.
[l] and [u] are off-diagonal matrices of [L] and [U], respectively.

This formulates a by-pass of the stage of computing matrix powers, and hence provides further speed up (e.g. decrease in) in the computing time. The search space in (ω̄, φ) now contains all positive real numbers. The best-fit (ω̄*, φ*) are defined at the zero-crossing condition; the corresponding completion efficiency and CF parameters are:

$$\lambda^* = (1 - \phi^* \Delta \lambda) \text{ and } \epsilon^* = \overline{\omega}^* \Delta \epsilon. \quad \text{Equation (8):}$$

Figure 6:
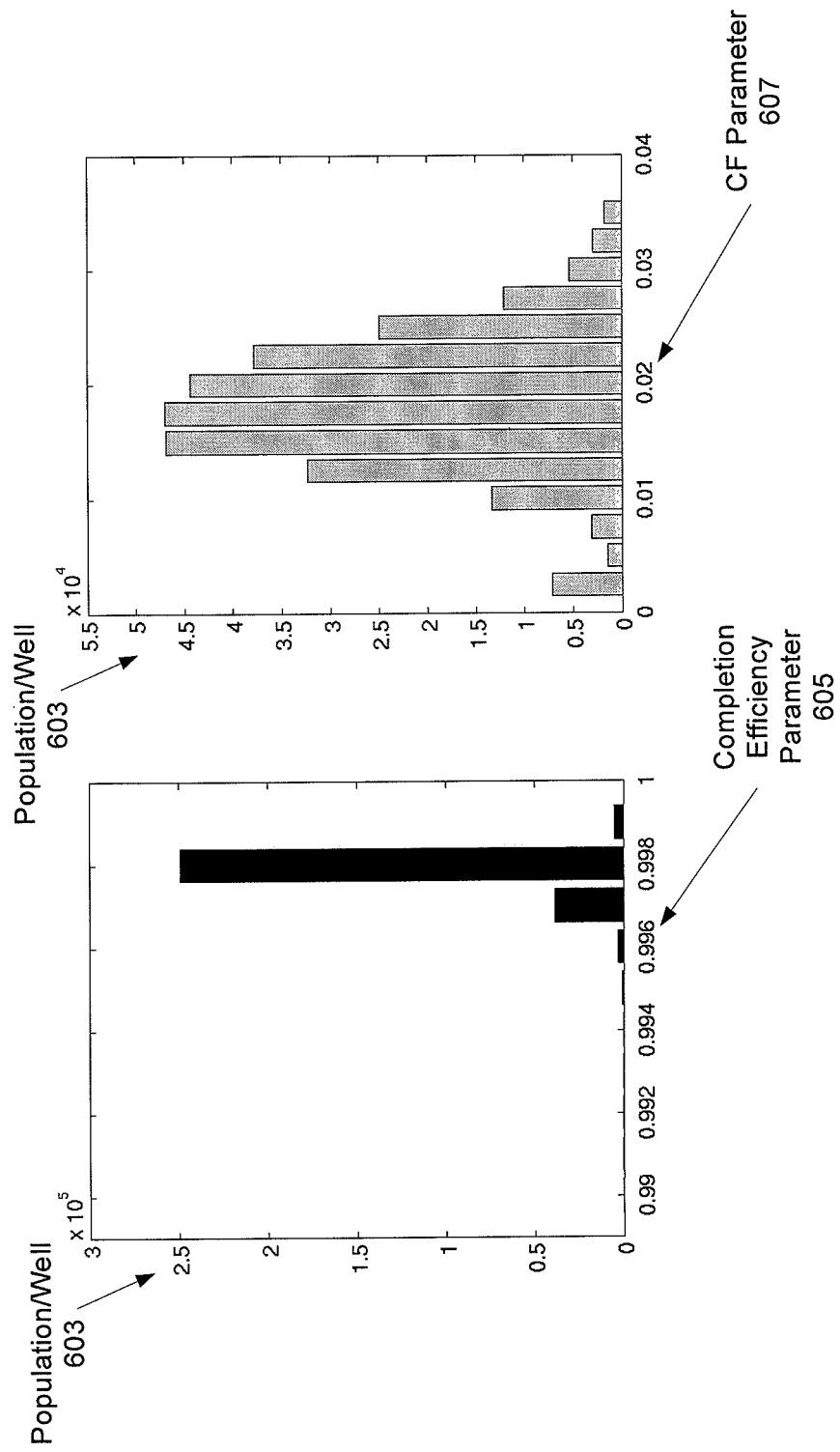
FIG. 6 is a simplified graphical representation of one embodiment of the distribution of parameter values across a sample of populations of substantially identical template molecules.

The embodiments presented above are based on constructing and inversing the matrices, and a two-dimensional search in the (ε, λ) plane to probe the optimal pair of CAFIE parameters. These calculations typically are performed on each population of substantially identical template molecules, which for example may include a site-by-site analysis in an array of reaction sites based system (e.g. such as a PicoTiter-Plate™ array of wells or ISFET array of wells). In some embodiments, a matrix is constructed for each population/site to produce optimal CAFIE values (ε*, λ*). FIG. 6 provides an illustrative example of the distribution of completion efficiency parameter 605 values λ* and CF parameter 607 values ε* in a sample of several hundred thousand populations/wells 603, as calculated by use of the inversion/search Method 1 described above. Calculation by use of the above-described Method 2, which requires less computational time than Method 1, provides similar results.

The embodiments described above also assume that the rates associated with the constant completion efficiency λ and CF ε parameters remain constant throughout the sequencing runs. This assumption can be alleviated by applying the CAFIE search and the inversion procedures on what may be referred to as "flow windows" in flowgrams that comprise several flow cycles (wherein "several" means any integer between 1 and the total number of flow cycles). For example, each flow window is a subset of the full set of flow cycles represented in a flowgram, with a pair of CAFIE parameters and a corresponding clean theoretical flowgram 101 needing to be found. In the present example, each flow window is arranged such that it starts from the first flow in the flowgram associated with a sequencing run and ends at a certain flow shorter or equal to the full length of the flow cycles in the flowgram, where each smaller flow window is nested within a larger one. For each flow window k, the search and inversion processes occur independently to produce a set of CAFIE parameters 113, which are now functions of window indices k: $\epsilon^* = \epsilon^*(k)$ and $\lambda^* = \lambda^*(k)$. The computed theoretical flowgram 101, p(k), also nested, is the result of these variable values of the CAFIE parameters depending on the indices k. A "stitching" process: p=p(k) for flows between windows (k−1) and k, re-assembles the flow window sequences p(k) into the final flowgram (p) 101.

In the same or alternative embodiments, the assumption of constant values for λ and ε may be eliminated by another method. For example, completion efficiency λ and CF ε parameters can assume parametric forms, such as exponentials, for each nucleotide species addition "N" ("A", "G", "C", or "T"), and as functions of flow position "i" (1, 2, 3, . . . ):

$$\lambda_N(i) = \lambda^0_N * \exp(-\delta_N * i),$$

$$\epsilon_N(i) = \epsilon^0_N * \exp(-\beta_N * i). \quad \text{Equations (9-10):}$$

Wherein:
$\lambda_N(i)$ is the completion efficiency of nucleotide species "N" at "i"-th flow
$\epsilon_N(i)$ is the CF of nucleotide species "N" at "i"-th flow
$\lambda^0_N$ and $\epsilon^0_N$ are the initial values
$\delta_N$ and $\beta_N$ are the attenuation rates Search methods are applied in the four parameter spaces, $\lambda^0_N, \epsilon^0_N, \delta_N$ and $\beta_N$, to determine the optimal values.

In addition, those of ordinary skill in the related art will also appreciate that other sources of noise not related to the described CAFIE mechanisms may exist. Such sources of noise may include, but are not limited to electronic sources such as what may be referred to as "Dark Current", optical sources, biological sources, chemical sources, or other sources known in the art or that may be discovered in the future. Some embodiments of the presently described invention may exhibit varying levels of sensitivity to the other sources of noise that may, in many applications, be at a substantially consistent and/or predictable level. For example, predictable and consistent levels of noise attributable to known or unknown sources are generally easy to correct. One method of correction is to mathematically add or subtract a value associated with the noise (depending upon whether the noise adds excess signal or reduces detected signal) from all signal values associated with a flow.

In some embodiments where the level of noise is not predictable, at least in part, estimations of the level of noise may be derived from information embedded in the signal data. For example, for nucleotide species known or predicted to not be present at a sequence position it is expected that the actual signal value should equal to zero (i.e. "zero-mer" position). Therefore, any detected signal may be attributable to all sources of noise in the system. In the present example, since the presently described embodiment estimates noise from CAFIE mechanisms such noise may be removed from the data and the underlying noise revealed. In the present example, the estimates may be improved by looking at all "zero-mer" sequence positions in a sequence run. In this case, the value of "threshold" in the binary encoding $p'^{(n)}$ Equation (4), can be dynamically determined for each run, to represent its noise level, instead of a fixed value as described in the previous embodiment above.

Even further, some previously described embodiments included what may be referred to as "safety criteria" to prevent over correction of the sequence data represented in an observed flowgram. As described above, over correction can cause an exponential accumulation of error introduced as the described algorithm iterates. For example, the other sources of noise described above may determine the safety criteria that include an amount of correction to be applied to the signal data. For example, some implementations may assume a given level of noise from other non-CAFIE sources and apply a safety criteria of what may be referred to as 60% correction (e.g. 100% implies full correction) to the data. This estimate uses a "hybrid" flowgram, "0.6p+0.4q", comprising 60% of the computed clean flowgram p and 40% of the observed flowgram q. Alternatively, if the non-CAFIE noise is at a "low" level a higher percentage of correction may be applied, such as for instance 80%.

EXAMPLE 1

Figure 7:
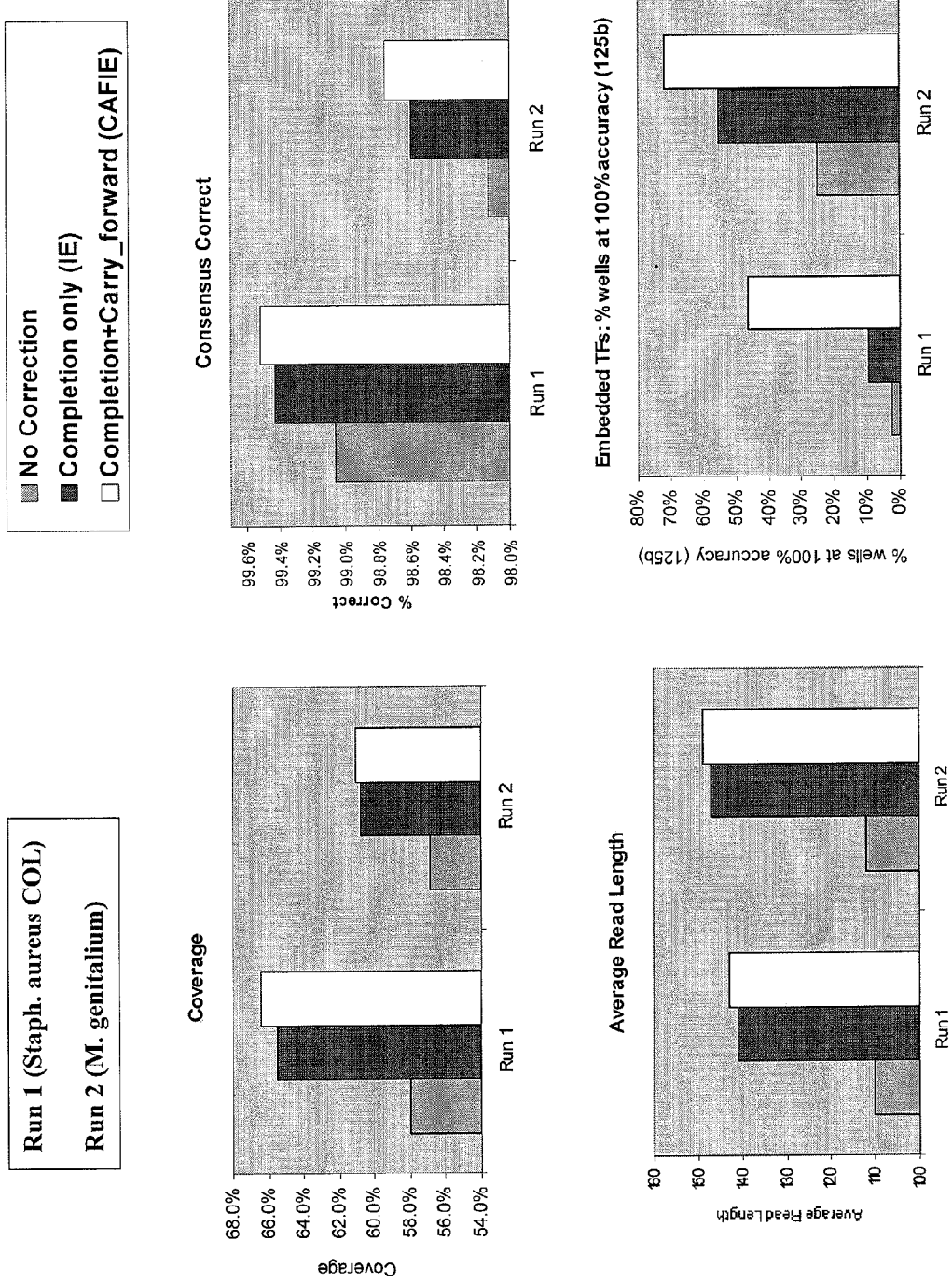
FIG. 7 is a simplified graphical representation of one embodiment of the effects of IE correction only, and the effects of CAFIE correction.

The genomes of *Staphylococcus aureus* COL and *Mycoplasma genitalium* were shotgun sequenced on a 454 Life Sciences Corporation Genome Sequencer (Margulies et al., 2005, incorporated by reference above). FIG. 7 provides an illustrative example of the effects of IE correction only and CAFIE correction on genome coverage, correctness of the consensus sequence, medium read length, and percentage of wells having achieved 100% accuracy of read lengths of over 125 sequence positions. By each of these measures, CAFIE correction was superior to IE correction alone. IE correction alone was superior to the results achieved without correction. Beads with control sequences were prepared separately and mixed with the experimental sample prior to preparation of the array.

As FIG. 7 demonstrates the use of the CAFIE correction procedures results in an increase of the average read length for a 63 flow cycle run from 112 sequence positions to 147 sequence positions which is near the theoretical maximum for 63 flow cycles or 252 flow iterations (e.g. each flow cycle includes 4 nucleotide species flow iterations). The theoretical maximum is computed by multiplying the number of flow cycles, 63 in this case, by the number of sequence positions (2.5) that are extended, on average, in each cycle of 4-nucleotide additions: 63×2.5=157.5 (theoretical maximum). The 147 sequence position average read length was determined by mapping the flowgrams to a known genome sequence, with 95% accuracy over the flow cycles.

Those of ordinary skill in the related art will appreciate that the accurate removal of error from data provides for a more efficient and accurate interpretation of said data. Thus, for instance, removing error from data generated in a sequencing run results in more accurate production of calls identifying each nucleic acid species in a sequence generated from a sequence run and higher quality sequence information. Some embodiments of the previously described invention include systems and methods for analyzing data generated from SBS sequencing runs on a sequencing apparatus. Some examples of SBS apparatus and methods may employ what may be referred to as a pyrophosphate based sequencing approach that may, for instance, comprise one or more of a detection device such as a charge coupled device (CCD) camera, a microfluidics chamber, a sample cartridge holder, or a pump and flow valves.

Embodiments of the presently described invention provide substantial performance improvements over the embodiments of CAFIE correction described above (hereafter referred to as "Standard CAFIE") providing significant advantages to users. As will be described in greater detail below the improved CAFIE correction methods extend upon the Standard CAFIE correction method described above by taking theoretical flowgram (p) output from Standard CAFIE and recursively re-estimating the flowgram signals until the positive incorporation list converges upon an optimized result (hereafter referred to as "Recursive CAFIE"). Upon convergence of the recursively corrected flowgram and the positive incorporation list, the Recursive CAFIE method yields better correction over the Standard CAFIE correction method described above as will be described in further detail below. The improvements comprise an improved algorithm for finding the phasic synchrony CAFIE parameters and a recursive procedure to correct the phasic synchrony errors. The same or alternative embodiments may include Reference CAFIE correction where a consensus flow list can be taken from an organism's known reference sequence and used to estimate the threshold value as described above where positions in the binary encoding list can be predicted to have no signal based upon the corresponding sequence position in the reference sequence and thus an observed signal may be attributed to noise and/or a sequence variant from the reference sequence. It will be appreciated that the magnitude of the observed signal is generally indicative of whether it can be attributed to a sequence variant or to noise, particularly when compared to the magnitude of signal at other positions in the binary encoding list that are predicted to have no signal.

Figure 8:
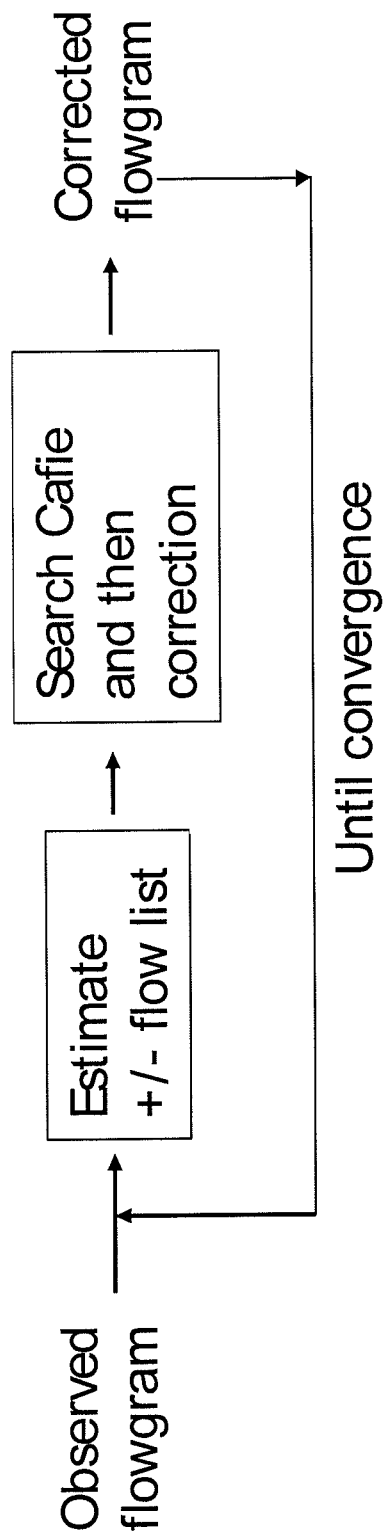
FIG. 8 is a simplified graphical representation of one embodiment of a method to recursively correct phasic synchrony errors in sequence data for n iterations.

FIG. 8 provides a simplified graphical example of a Recursive CAFIE embodiment that iteratively develops a more accurate flow list by further optimizing the CAFIE parameters, and re-applying the further optimized parameters producing intermediate CAFIE-corrected flowgrams ultimately converging upon a recursively corrected flowgram.

Typical embodiments of a Recursive CAFIE correction strategy first performs phasic synchrony correction on an observed flowgram from a sequence read using the Standard CAFIE correction method, and through iterations using the Recursive CAFIE algorithm producing CAFIE-corrected flowgrams, it estimates a new binary encoding list (p') which more accurately reflects the true sequence than what was derived from the observed flowgram. The new binary encoding list is then used to estimate again (and thus more accurately) the completion efficiency $\lambda$, and carry-forward $\epsilon$ parameters for the sequence read. The new estimation of $(\lambda, \epsilon)$ is achieved by demanding that the corrected signals in the negative incorporation events of the binary encoding list be as close to the actual background noise level as possible. Specifically, we perform perturbations of parameters $\lambda$ and $\epsilon$ on the CAFIE matrix in the algorithm:

$$\Delta q_\lambda = [M^{-1}(p', 1-\Delta\lambda, 0)]*q - q,$$

$$\Delta q_\epsilon = [M^{-1}(p', 1-\Delta\epsilon)]*q - q, \quad \text{Equations (11-12):}$$

where $M(p', \lambda, \epsilon)$ is the CAFIE matrix described above, $\Delta q_\lambda$ and $\Delta q_\epsilon$ are the changes of the flowgram in response to perturbations $\Delta\lambda$ and $\Delta\epsilon$ with the binary encoding list p', and p is the theoretical flowgram computed by the Standard CAFIE correction.

In the recursive CAFIE method, new $\lambda$ and $\epsilon$ are obtained by the following procedure: The perturbation increments ($t_\lambda$, $t_\epsilon$) are computed by minimizing the following expression:

$$\arg(t_\lambda, t_\varepsilon) \sum_i |q(i) + t_\lambda \Delta q_\lambda(i) + t_\varepsilon \Delta q_\varepsilon(i) - \text{noise}|^2 \quad \text{Equation (13)}$$

for $i$ that $p'(i) = 0$ where noise is the average of the flow signals associated with negative incorporation events (p'(i)=0) of the first 48 flows. After the values of $t_\lambda$ and $t_\varepsilon$ are determined the CAFIE correction parameters ($\lambda$, $\varepsilon$) are computed as:

$$\lambda = 1 - t_\lambda \Delta \lambda,$$

$$\varepsilon = t_\varepsilon \Delta \varepsilon. \quad \text{Equations (14-15):}$$

In this way, the $\lambda$ and $\varepsilon$ are ensured as the optimal pair that minimizes the out-of-phase CAFIE error. Finally, the CAFIE correction is performed $$p^{(1)} = [M^{-1}(p', \varepsilon, \lambda)] * q, \quad \text{Equation (16):}$$

to obtain a new CAFIE-corrected theoretical flowgram $p^{(1)}$.

The above-stated procedure is repeated iteratively: at iteration n+1, the flowgram $p^{(n)}$ is used to estimate the binary encoding list $p'^{(n)}$, perform again CAFIE search by the minimization procedure (13), and obtain through the perturbation formulae (14-16) a new CAFIE-corrected flowgram $p^{(n+1)}$ and CAFIE parameters ($\varepsilon^{(n+1)}$, $\lambda^{(n+1)}$)

$$p^{(n+1)} = [M^{-1}(p^{(n)}, \varepsilon^{(n+1)}, \lambda^{(n+1)})] * q. \quad \text{Equation (17):}$$

In some embodiments the recursive procedure continues until the binary encoding list converges, $p'^{(n+1)} = p'^{(n)}$. The positive flow list i, where $p'^{(n)}(i)=1$, approximates the flow positions that show positive nucleotide incorporation. The more accurately the positive flow list is estimated by the algorithm results in a more accurate correction of phasic asynchrony. Thus the recursive algorithm uses the CAFIE-corrected flowgram iteratively resulting in a recursively corrected flowgram at convergence; at each iteration the algorithm obtains a better estimation for the CAFIE parameters ($\varepsilon^{(n)}$, $\lambda^{(n)}$) and binary encoding $p'^{(n)}$ which gives more accurate CAFIE correction for the phase errors in the next iteration.

In some embodiments the recursive procedure continues until the CAFIE parameters converges, ($\varepsilon^{(n+1)}, \lambda^{(n+1)}$)=($\varepsilon^{(n)}, \lambda^{(n)}$) which also indicates convergence of the binary encoding list by the nature of how the binary encoding list is calculated using the CAFIE parameters. One advantage of using the CAFIE parameters to determine convergence is that it is computationally more efficient than estimating convergence of the binary encoding list p'.

Figure 9:
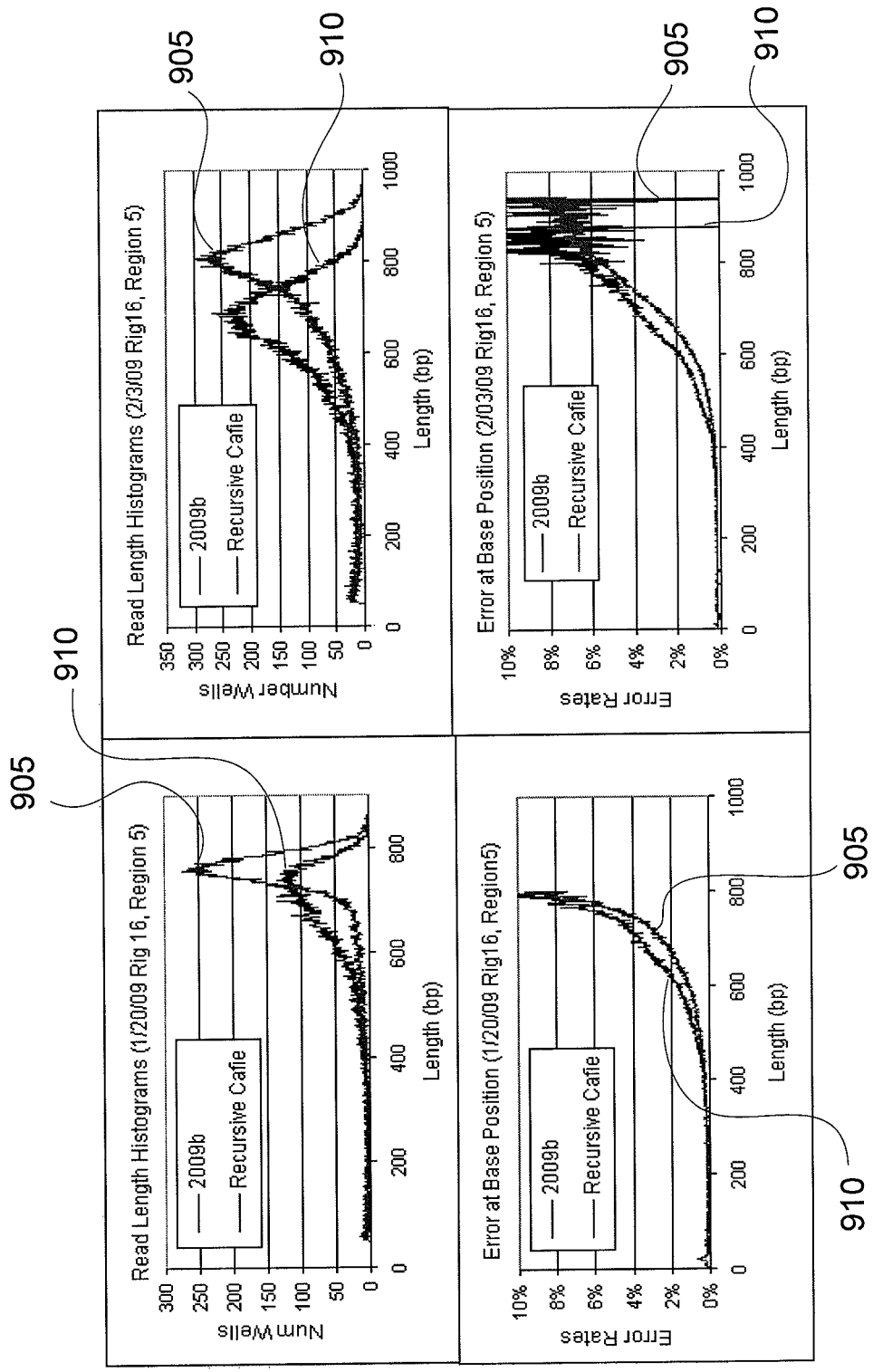
FIG. 9 is a simplified graphical representation of one embodiment of sequencing results showing advantages over previously described embodiments for read length and error at base position utilizing the recursive algorithm for correction of phasic synchrony errors in sequence data.

Tables 1-6 present a comparison of results between the Standard CAFIE and the Recursive CAFIE correction methods for sequence reads. In all of these, testing the Recursive CAFIE correction method was able to deliver 50-90 bp longer read lengths, higher number of High Quality reads (defined as reads that pass a quality trimming process) and comparable read accuracy as compared to Standard CAFIE correction strategies. FIG. 9 also provides an exemplary plot of the read length and the read error distributions for the two CAFIE correction methods, showing favorable results from Recursive CAFIE correction line 905 over the Standard CAFIE method line 910. Table 5 summarizes the results of 8 sequencing runs processed with the recursive correction method; the average mapped lengths are at 600-700 bp; Q20 read lengths 430-565 bp, longest perfect read lengths 870-930 bp, and longest mapped reads 901-997 bp.

TABLE 1

Comparison of results of Recursive CAFIE and Standard CAFIE methods for two Sequencing runs.

| | Run | | | |
|---|---|---|---|---|
| | Region 5, *E. coli* | | Region 5, *E. coli* | |
| | CAFIE Correction | | | |
| | Standard | Recursive | Standard | Recursive |
| Mapped Reads | 22,655 | 22,356 | 53,920 | 53,807 |
| Mapped Bases | 13,642,363 | 15,303,508 | 30,530,577 | 35,996,290 |
| Cumul. Err 500B | 0.24% | 0.19% | 0.29% | 0.21% |
| Err at 500B | 0.76% | 0.50% | 0.86% | 0.55% |
| Inf Read Error | 0.54% | 0.56% | 0.57% | 0.69% |
| Last 100 Base IRE | 2.25% | 2.55% | 2.22% | 3.08% |
| Avg. Map Length | 602 | 684 | 566 | 668 |
| Read Length at Mode | 685 | 762 | 597 | 749 |
| 7mer Accuracy | 80.33% | 79.70% | 80.01% | 80.96% |
| largeContigMetrics | | | | |
| numberOfContigs | 1276 | 947 | 204 | 116 |
| numUndercalls | 2554 | 3219 | 716 | 703 |
| numOvercalls | 6805 | 4964 | 1625 | 967 |
| consensusAccuracy | 99.7826% | 99.8141% | 99.9490% | 99.9637% |

TABLE 2

Comparison of Recursive CAFIE and Standard CAFIE correction methods:

| | Region, Genome | | | |
|---|---|---|---|---|
| | 1, *C. jejuni* | | 5, *E. coli* | |
| | CAFIE Correction | | | |
| | Standard | Recursive | Standard | Recursive |
| Mapped Reads | 21,399 | 20,768 | 18,481 | 18,081 |
| Mapped Bases | 11,207,003 | 12,821,276 | 10,246,089 | 11,693,521 |
| Cumul. Err 500B | 0.58% | 0.43% | 0.30% | 0.22% |
| Err at 500B | 2.22% | 1.58% | 1.00% | 0.72% |
| Inf Read Error | 0.88% | 1.00% | 0.54% | 0.60% |
| Last 100 Base IRE | 2.99% | 3.24% | 2.13% | 2.29% |
| Avg. Map Length | 523 | 617 | 554 | 646 |
| Read Length at Mode | 574 | 680 | 649 | 666 |
| 7mer Accuracy | 78.52% | 76.40% | 78.51% | 78.85% |
| largeContigMetrics | | | | |
| numberOfContigs | 72 | 46 | 1901 | 1474 |
| numUndercalls | 467 | 615 | 3451 | 5123 |
| numOvercalls | 803 | 775 | 8885 | 7099 |
| consensusAccuracy | 99.9214% | 99.9142% | 99.6939% | 99.7091% |

TABLE 3

Comparison of Recursive CAFIE and Standard CAFIE correction methods:

| | Region, Genome | | | |
|---|---|---|---|---|
| | 1, *E. coli* | | 2, *E. coli* | |
| | CAFIE Correction | | | |
| | Standard | Recursive | Standard | Recursive |
| Mapped Reads | 24,124 | 24,752 | 142,366 | 142,428 |
| Mapped Bases | 14,579,291 | 16,445,958 | 80,411,965 | 90,347,333 |
| Cumul. Err 500B | 0.31% | 0.22% | 0.38% | 0.27% |
| Err at 500B | 1.14% | 0.77% | 1.40% | 0.81% |
| Inf Read Error | 0.74% | 0.72% | 0.77% | 0.68% |
| Exp Read Error | 0.85% | 0.55% | 0.86% | 0.62% |
| Last 100 Base IRE | 3.37% | 3.08% | 3.29% | 2.71% |
| Avg. Map Length | 604 | 664 | 564 | 634 |
| 7mer Accuracy | 80.33% | 78.52% | 81.18% | 80.54% |
| largeContigMetrics | | | | |
| numberOfContigs | 1061 | 776 | 36 | 24 |
| numUndercalls | 2839 | 3808 | 136 | 114 |
| numOvercalls | 9186 | 6143 | 260 | 171 |
| consensusAccuracy | 99.7249% | 99.7766% | 99.9914% | 99.9938% |

TABLE 4

Comparison of Recursive CAFIE and Standard CAFIE correction methods

| | Region, Genome | | | |
|---|---|---|---|---|
| | 1, *E. coli* | | 2, *E. coli* | |
| | CAFIE Correction | | | |
| | Standard | Recursive | Standard | Recursive |
| Mapped Reads | 25377 | 26609 | 131653 | 131528 |
| Mapped Bases | 14896516 | 16368514 | 70280071 | 73892785 |
| Cumulative Err Base 500 | 0.33% | 0.23% | 0.47% | 0.32% |
| Err at Base 500 | 1.43% | 0.89% | 1.59% | 0.84% |
| Inf Read Error | 0.80% | 0.60% | 0.88% | 0.59% |
| Last 100 Base IRE | 3.68% | 2.49% | 3.44% | 1.96% |
| Avg. Map Length | 587 | 615 | 533 | 561 |
| 7mer Accuracy | 80.80% | 82.82% | 76.96% | 79.91% |
| largeContigMetrics | | | | |
| numberOfContigs | 1069 | 838 | 47 | 38 |
| numUndercalls | 3703 | 2720 | 134 | 127 |
| numOvercalls | 8866 | 5329 | 278 | 162 |
| consensusAccuracy | 99.7140% | 99.8193% | 99.9911% | 99.9937% |

TABLE 5

Summary of results for the recursive CAFIE correction for 8 Sequencing runs.

| Run | Reg | Avg Map L | Mode | 7-mer Acc. | 400b Error @ | Cumm | 600b Error @ | Cumm | Q20 | Perfect RL | Long Map |
|---|---|---|---|---|---|---|---|---|---|---|---|
| 1/20, Rig 16* | 5 | 692 | 758 | 80.60% | 0.23% | 0.18% | 1.17% | 0.30% | 590 | 841 | 867 |
| 2/3, Rig 16 | 5 | 697 | 807 | 79.3% | 0.26% | 0.19% | 1.18% | 0.32% | 578 | 936 | 982 |
| 3/10, Rig 16 | 4 | 658 | 717 | 79.0% | 0.30% | 0.20% | 1.02% | 0.33% | 571 | 906 | 953 |
|  | 7 | 645 | 722 | 71.6% | 0.44% | 0.19% | 1.82% | 0.42% | 519 | 875 | 944 |
| 7/22, Rig 21 | 1 | 683 | 775 | 77.9% | 0.65% | 0.21% | 1.83% | 0.42% | 533 | 908 | 986 |
|  | 2 | 661 | 702 | 75.7% | 0.42% | 0.21% | 1.58% | 0.37% | 565 | 901 | 942 |
|  | 3 | 656 | 669 | 75.0% | 0.44% | 0.20% | 1.21% | 0.36% | 560 | 919 | 940 |
| 7/22, SC18 | 1** | 656 | 712 | 75.9% | 0.68% | 0.32% | 3.37% | 0.76% | 432 | 923 | 997 |
|  | 5 | 673 | 702 | 78.3% | 0.37% | 0.17% | 1.56% | 0.37% | 534 | 896 | 954 |
| 7/23, Rig 21 | 2 | 647 | 725 | 71.9% | 0.55% | 0.23% | 2.02% | 0.46% | 510 | 905 | 940 |
|  | 3 | 658 | 725 | 73.3% | 0.37% | 0.20% | 1.64% | 0.37% | 558 | 930 | 936 |
|  | 5 | 624 | 668 | 77.2% | 0.37% | 0.21% | 1.39% | 0.36% | 561 | 871 | 901 |
| 7/23, SC18 | 1 | 659 | 709 | 80.3% | 0.36% | 0.17% | 1.77% | 0.39% | 531 | 883 | 937 |
|  | 5 | 661 | 676 | 76.3% | 0.35% | 0.16% | 1.43% | 0.37% | 534 | 886 | 939 |
| 7/30, SC18 | 2 | 684 | 725 | 76.40% | 0.31% | 0.15% | 2.18% | 0.42% | 519 | 862 | 947 |
|  | 3 | 682 | 725 | 75.30% | 0.35% | 0.15% | 2.33% | 0.42% | 519 | 833 | 923 |
|  | 6 | 685 | 722 | 76.50% | 0.38% | 0.15% | 2.25% | 0.44% | 507 | 886 | 942 |
|  | 7 | 680 | 722 | 76.20% | 0.44% | 0.15% | 2.38% | 0.45% | 504 | 851 | 920 |

*300 cyc run
**CJ, all other E coli
Avg Map L: 600-700 bp; Q20 RL: 430-565 bp
Longest Perfect RL: 870-930 bp; Longest Mapped Read: 901-997 bp Thus, it is seen that methods and systems are provided for correcting errors in sequence data obtained during the sequencing of nucleic acids. Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other unclaimed inventions are also contemplated. The right to pursue such inventions in later claims is hereby reserved.

What is claimed is:

1. A method for recursively correcting an error associated with phasic synchrony of nucleic acid sequence data generated from a population of substantially identical copies of a template molecule, comprising:
   (a) detecting a plurality of signals generated in response to a plurality of nucleotide species introduced during a sequencing reaction;
   (b) generating an observed value for the signal detected from each of the nucleotide species;
   (c) defining a plurality of positive incorporation values and a plurality of negative incorporation values from the observed values using a carry forward value and an incomplete extension value;
   (d) simultaneously calculating a carry forward perturbation increment and an incomplete extension perturbation increment;
   (e) revising the carry forward value and the incomplete extension value using the carry forward perturbation increment and the incomplete extension perturbation increment;
   (f) re-defining the plurality of positive incorporation values and the plurality of negative incorporation values using the revised carry forward value and the revised incomplete extension value; and
   (g) repeating steps (d)-(f) until convergence of the plurality of positive incorporation values and the plurality of negative incorporation values, thereby generating a corrected nucleic acid sequence read.

2. The method of claim 1, wherein:
the positive incorporation value and the negative incorporation value are integers.

3. The method of claim 2, wherein:
the positive incorporation value is a 1 and the negative incorporation value is a 0.

4. The method of claim 1, wherein:
prior to step (c) the positive incorporation values and the negative incorporation values are assigned using a threshold value, wherein the positive incorporation value is assigned when the observed value is above the threshold value and the negative incorporation value is assigned when the observed value is below the threshold value.

5. The method of claim 4, wherein:
the threshold value comprises a value in the range between 0 and 1.

6. The method of claim 5, wherein:
the threshold value is 0.2.

7. The method of claim 1, wherein:
the positive incorporation values and the negative incorporation values are defined by using a reference sequence to predict a plurality of positions where no nucleotide species is present.

8. The method of claim 1, wherein:
a plurality of the sequencing reactions are executed in parallel, wherein steps (a)-(g) are executed for each of the sequencing reactions.

9. A method for recursively correcting an error associated with phasic synchrony of nucleic acid sequence data generated from a population of substantially identical copies of a template molecule, comprising the steps of:
(a) detecting a plurality of signals generated in response to a plurality of nucleotide species introduced during a sequencing reaction;
(b) generating an observed value for the signal detected from each of the nucleotide species;
(c) defining a plurality of positive incorporation values and a plurality of negative incorporation values from the observed values using a carry forward value and an incomplete extension value;
(d) simultaneously calculating a carry forward perturbation increment and an incomplete extension perturbation increment;
(e) revising the carry forward value and the incomplete extension value using the carry forward perturbation increment and the incomplete extension perturbation increment;
(f) re-defining the plurality of positive incorporation values and the plurality of negative incorporation values using the revised carry forward value and the revised incomplete extension value; and
(g) repeating steps (d)-(f) until convergence of the carry forward value and the incomplete extension value, thereby generating a corrected nucleic acid sequence read.

10. A system for recursively correcting an error associated with phasic synchrony of nucleic acid sequence data generated from a population of substantially identical copies of a template molecule, comprising:
(a) a sequencing instrument that detects a plurality of signals generated in response to a plurality of nucleotide species introduced during a sequencing reaction;
(b) a computer comprising executable code stored thereon which performs a method comprising the steps of:
 i. generating an observed value for the signal detected from each of the nucleotide species;
 ii. defining a plurality of positive incorporation values and a plurality of negative incorporation values from the observed values using a carry forward value and an incomplete extension value;
 iii. simultaneously calculating a carry forward perturbation increment and an incomplete extension perturbation increment;
 iv. revising the carry forward value and the incomplete extension value using the carry forward perturbation increment and the incomplete extension perturbation increment;
 v. re-defining the plurality of positive incorporation values and the plurality of negative incorporation values using the revised carry forward value and the revised incomplete extension value; and
 vi. repeating steps iii-v until convergence of the carry forward value and the incomplete extension value, thereby generating a corrected nucleic acid sequence read.

11. The system of claim 10, wherein:
the positive incorporation value and the negative incorporation value are integers.

12. The system of claim 11, wherein:
the positive incorporation value is a 1 and the negative incorporation value is a 0.

13. The system of claim 10, wherein:
prior to step (ii) the computer assigns the positive incorporation values and the negative incorporation values using a threshold value, wherein the positive incorporation value is assigned when the observed value is above the threshold value and the negative incorporation value is assigned when the observed value is below the threshold value.

14. The system of claim 13, wherein:
the threshold value comprises a value in the range between 0 and 1.

15. The system of claim 14, wherein:
the threshold value is 0.2.

16. The system of claim 10, wherein:
the computer defines the positive incorporation values and the negative incorporation vales using a reference sequence to predict a plurality of positions where no nucleotide species is present.

17. The system of claim 10, wherein:
the sequencing system executes a plurality of the sequencing reactions in parallel, wherein the computer executes steps (i)-(vi) for each of the sequencing reactions.

* * * * *

UNITED STATES PATENT AND TRADEMARK OFFICE
CERTIFICATE OF CORRECTION

PATENT NO. : 9,317,654 B2
APPLICATION NO. : 13/718852
DATED : April 19, 2016
INVENTOR(S) : Yi-Ju Chen et al.

Page 1 of 1

It is certified that error appears in the above-identified patent and that said Letters Patent is hereby corrected as shown below:

In the claims

Column 30, line 36, in claim 16:

"the negative incorporation vales"

should read

--the negative incorporation values--

Signed and Sealed this
Twelfth Day of July, 2016

Michelle K. Lee
*Director of the United States Patent and Trademark Office*